United States Patent [19]

Mochida et al.

[11] Patent Number: 5,077,410

[45] Date of Patent: Dec. 31, 1991

[54] INTERMEDIATE COMPOUNDS OF 1-ACYL-2,3-DIHYDRO-4(1H)-QUINOLINONE-4-OXIME DERIVATIVES

[75] Inventors: Ei Mochida, Toshima; Akio Uemura; Kazuo Kato, both of Mishima; Hiroki Tokunaga, Tokyo; Akinori Haga, Kawasaki, all of Japan

[73] Assignees: Mochida Pharmaceutical Co., Ltd.; Hodogaya Chemical Co., Ltd., both of Tokyo, Japan

[21] Appl. No.: 301,125

[22] Filed: Jan. 25, 1989

Related U.S. Application Data

[62] Division of Ser. No. 42,784, Apr. 27, 1987, Pat. No. 4,839,368.

[30] Foreign Application Priority Data

May 2, 1986 [JP] Japan .................... 61-102847
Apr. 15, 1987 [JP] Japan .................... 62-92788

[51] Int. Cl.⁵ .................... C07D 215/48; C07D 401/06
[52] U.S. Cl. .................... 546/156; 544/337; 544/405; 544/406; 546/23; 546/153; 546/159
[58] Field of Search .................... 546/156

[56] References Cited

U.S. PATENT DOCUMENTS

| | | | |
|---|---|---|---|
| 3,976,650 | 8/1976 | Johnson | 546/156 |
| 4,013,662 | 3/1977 | Harbert | 546/156 |
| 4,260,764 | 4/1981 | Johnson | 546/153 |
| 4,421,919 | 12/1983 | Jinbo et al. | 546/159 |
| 4,521,607 | 6/1985 | Oka et al. | 549/39 |
| 4,675,324 | 6/1987 | Ueda et al. | 546/82 |
| 4,736,055 | 4/1988 | Dietliker et al. | 544/159 |
| 4,767,780 | 8/1988 | Ueda et al. | 548/370 |
| 4,839,368 | 6/1989 | Mochida et al. | 514/313 |

FOREIGN PATENT DOCUMENTS

| | | |
|---|---|---|
| 1189078 | 6/1985 | Canada . |
| 163888 | 12/1985 | European Pat. Off. . |
| 180352 | 5/1986 | European Pat. Off. . |
| 2487346 | 1/1982 | France . |
| 176282 | 1/1976 | New Zealand . |
| 2081091 | 2/1982 | United Kingdom . |

OTHER PUBLICATIONS

Bekhli et al., Chemical Abstracts, vol. 87, No. 133435 (1977).
Hayashi et al, Chemical Abstracts, vol. 84, No. 89971 (1976).
Crabb et al, *J. Chem. Soc, Perkin Trans. I*, p. 1381 (1985).
Janzso et al., Chemical Abstracts, vol. 85, No. 108503 (1976).
Bradley et al., *J. Chem. Soc, Perkin Trans I*, p. 2019 (1972).
Moravcsik et al, Chemical Abstracts, vol. 99, No. 54065 (1983).
Misiti et al, *J. Het. Chem*, 8, p. 231 (1971).
Mochida et al, Chemical Abstracts, vol. 108, No. 204508 (1988).
Ueda et al., Chemical Abstracts, vol. 105, No. 78931 (1986).
Badea et al., Chemical Abstracts, vol. 89, No. 109137 (1978).
Bekhli et al., Chemical Abstracts, vol. 84, No. 4800 (1976).
Collins et al., Chemical Abstracts, vol. 54, No. 22646d (1960).

*Primary Examiner*—Mukund J. Shah
*Assistant Examiner*—E. Bernhardt
*Attorney, Agent, or Firm*—Oliff & Berridge

[57] ABSTRACT

The present invention relates to intermediate compounds to produce novel 1-acyl-2,3-dihydro-4(1H)-quinolinone-4-oxime derivatives with potent diuretic activity that can be used for treating and/or preventing hypertension, oedema and/or for removing ascites.

The present invention is based on two characters. One is the selection of acyl substituents of 2,3-dihydro-4(1H)-quinolinone at 1-position, namely propionyl, t-butylcarbonyl, benzoyl, 2-bromobenzoyl, 4-chlorobenzoyl, 2-methylbenzoyl, 2-ethylbenzoyl, 2,3-dimethoxybenzoyl, 2,4-dichlorobenzoyl, 4-chloro-2-methyl benzoyl or 2-chloro-4-nitrobenzoyl. The other is the selection of substituents and positional specificity at 6- or 7-position, namely halogen atom, methoxy, trifluoromethyl or dimethylamino group.

1-acyl-2,3-dihydro-4(1H)-quinolinone-4-oxime derivatives which are made from the intermediate compounds of the present invention have potent hypotensive, antioedematous and diuretic effect as well as an activity to remove ascites, and are extremely useful for the treatment of diseases and disorders mentioned above.

15 Claims, No Drawings

INTERMEDIATE COMPOUNDS OF 1-ACYL-2,3-DIHYDRO-4(1H)-QUINOLINONE-4-OXIME DERIVATIVES

This is a division of application Ser. No. 07/042,784 filed Apr. 27, 1987 now U.S. Pat. No. 4,839,368.

BACKGROUND OF THE INVENTION

The present invention relates to novel 1-acyl-2,3-dihydro-4(1H)-quinolinone-4-oxime derivatives, processes for producing said derivatives, intermediate compounds, novel 1-acyl-2,3-dihydro-4(1H)-quinolinone derivatives, to produce said derivatives, processes to produce said intermediate compounds, and compositions containing said derivatives with potent diuretic activity that can be used for treating and/or preventing hypertension, oedema and/or for removing ascites.

For the treatment of hypertension, benzothiazide derivatives or so-called loop diuretics have been widely used to lower blood pressure. These agents act mainly on the distal part of renal tubule or the loop of Henle and increase renal excretion of electrolytes and water. Many of these diuretics, however, are known to show several adverse reactions in common, for example, hypokalemia, hyperuricemia, decrease in sugar tolerance and disorder in lipid metabolism.

Diuretic agents have also been used for the treatment of oedema resulting from retention of water and electrolytes based on cardiac or renal insufficiency or on metabolic disorders, but such conventionally used diuretics show only marginal efficacy against retention of ascites which is often observed in the patients with abdominal tumor or liver cirrhosis.

These benzothiazide diuretics and loop diuretics are known to share common chemical substructures.

From the foregoing background, it has been desired to develop novel diuretics that are useful in the treatment of hypertension, oedema and removal of ascites and that do not cause the aforementioned adverse reactions by synthesizing compounds whose chemical structures are novel and different from those of known diuretics.

SUMMARY OF THE INVENTION

An object of the present invention is to provide novel 1-acyl-2,3-dihydro-4(1H)-quinolinone-4-oxime derivatives and salts thereof, solvates of said derivatives and solvates of said salts.

Another object of the present invention is to provide processes for producing novel 1-acyl-2,3-dihydro-4(1H)-quinolinone-4-oxime derivatives.

A further object of the present invention is to provide compositions for treating hypertension, oedema and ascites which comprise novel 1-acyl-2,3-dihydro-4(1H)-quinolinone-4-oxime derivatives as active components.

A further object of the present invention is to provide intermediate compounds, novel 1-acyl-2,3-dihydro-4(1H)-quinolinone derivatives, in the synthesis of 1-acyl-2,3-dihydro-4(1H)-quinolinone-4-oxime derivatives and processes for producing such intermediate compounds.

The present invention is based on the selection of 1-acyl-2,3-dihydro-4(1H)-quinolinone-4-oxime derivatives, namely 0-sulfate, 0-mesylate, 0-methylphosphate and 0-carboxymethyl ether, especially 0-sulfate of 4-oxime.

The compounds of the present invention containing these substituents have potent hypotensive, antioedematous and diuretic effect as well as an activity to remove ascites and are extremely useful for the treatment of diseases and disorders mentioned above.

DETAILED DESCRIPTION OF THE INVENTION

As a result of extensive investigations concerning development of novel dihydroquinolinone oxime derivatives having a satisfactory diuretic activity, the present inventors have found that 1-acyl-2,3-dihydro-4(1H)-quinolinone-4-oxime derivatives, especially 1-acyl-2,3-dihydro-4(1H)-quinolinone-4-oxime-0-sulfate possesses a potent diuretic activity that can be used for treating and/or preventing hypertension, oedema and/or for removing ascites, thus satisfy these requirements and, have accomplished the present invention.

The present invention is directed to 1-acyl-2,3-dihydro-4(1H)-quinolinone-4-oxime derivatives represented by the general formula (I):

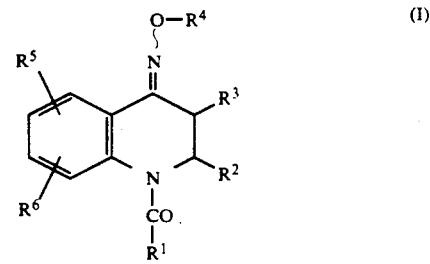

wherein $R^1$ represents an alkyl group of straight or branched chain containing 1 to 8 carbon atoms, a halogenated alkyl group of straight or branched chain containing 1 to 4 carbon atoms, a cycloalkyl group containing 3 to 6 carbon atoms, a lower alkyloxy group, a methoxymethyl group, a methoxycarbonylethyl group, a benzyl group, a styryl group, a naphthyl group, a pyridyl group, a thienyl group, a pyrazinyl group, a phenyl group or a phenyl group substituted with 1 to 5 substituents which are the same or different and selected from a group consisting of an alkyl group of straight or branched chain containing 1 to 4 carbon atoms, a hydroxyl group, a nitro group, a lower alkyloxy group, a trifluoromethyl group and a halogen atom, $R^2$ and $R^3$ are the same or different and represent hydrogen atoms or methyl groups, $R^4$ represents a carboxymethyl group, a sulfo group, a methanesulfonyl group or a methoxyphosphoryl group, $R^5$ and $R^6$ are the same or different and represent hydrogen atoms, halogen atoms, hydroxyl groups, methylthio groups, methylsulfinyl groups, methanesulfonyl groups, N,N-dimethylamino groups, nitro groups, acetyl groups, methyl groups, trifluoromethyl groups, methoxycarbonyl groups or methoxy groups, and the bond shown with a wavy line represents a bond of anti-form or syn-form, and a salt thereof as well as a solvate of said derivative and a solvate of said salt.

The present invention is also directed to a process for preparing above-mentioned 1-acyl-2,3-dihydro-4(1H)-quinolinone-4-oxime derivatives. The present invention is further directed to pharmaceutical compositions for treating hypertension, oedema and removal of ascites characterized by containing these 1-acyl-2,3-dihydro- 4(1H)-quinolinone-4-oxime derivatives as active components.

The present invention is also directed to intermediate compounds, novel 1-acyl-2,3-dihydro-4(1H)-quinolinone derivatives, in the synthesis of 1-acyl-2,3-dihydro-4(1H)-quinolinone-4-oxime derivatives and processes for producing such intermediate compounds.

The compounds of the present invention represented by the general formula (I) is chemically novel and can generally be produced according to the methods described below.

For example, known 2,3-dihydro-4(1H)-quinolinone or its derivatives, such as 5-chloro-2,3-dihydro-4-(1H)-quinolinone and 7-chloro-2,3-dihydro-4(1H)-qui nolinone (French Patent No. 1,514,280), 6-chloro-2,3-dihydro-4(1H)-quinolinone (The Journal of American Chemical Society, volume 71, page 1901-1904 (1949) and U.S. Pat. No. 2,558,211) and 8-chloro-2,3-dihydro-4(1H)-quinolinone (French Patent No. 1,514,280), or novel mono- or di-substituted 2,3-dihydro-4(1H)-quinolinones, which can generally be prepared by reacting known mono- or di-substituted aniline with γ-butyrolactone or with acrylic acid and subjecting the resultant N-carboxyethylated aniline with mono- or di-substitution(s) to cyclocondensation by Friedel-Crafts reaction (described in Step 1 of Example 8; the products therefrom are listed in Table 8), such as 6-chloro-7-fluoro-2,3-dihydro-4(1H)-quinolinone, 7-chloro-6-fluoro-2,3-dihydro-4(1H)-quinolinone and 6,7-difluoro-2,3-dihydro-4(1H)-quinolinone are reacted with reactive derivatives of carboxylic acids to be introduced as the acyl moiety, preferably acid halides, in organic solvents and, if necessary and desired, in the presence of deacidifying agents to obtain 1-acyl-2,3-dihydro-4(1H)-quinolinone derivatives as intermediate compounds.

As the organic solvent, chloroform, dichloromethane, ether, tetrahydrofuran, dioxane, benzene or ethyl acetate may be used; as the deacidifying agent, organic bases such as pyridine, triethylamine or N,N-dimethylaniline, or inorganic bases such as potassium carbonate, sodium carbonate or sodium bicarbonate may be used. As the acid halides, acid halides corresponding to $R^1$ in the general formula (I), such as 2-methylbenzoyl chloride, 2,4-dichlorobenzoyl chloride, 2-bromobenzoyl chloride, 4-chlorobenzoyl chloride, 2,2-dimethylpropionyl chloride or propionyl bromide may be used.

The intermediate compounds thus obtained, 1-acyl-2,3-dihydro-4(1H)-quinolinone derivatives, are reacted with hydroxylamine in organic solvents such as methanol, ethanol, tetrahydrofuran or dimethylformamide to obtain corresponding 1-acyl-2,3-dihydro-4(1H)-quinolinone-4-oximes, which are then reacted with sulfonating agents such as sulfur trioxide-pyridine complex or sulfur trioxide-dimethylformamide complex, or with halogenated phosphoric acid esters such as methyl dichlorophosphate in the presence of bases such as n-butyllithium, sodium hydride or phenyllithium, or with halogenated acetic acid or its ester such as bromoacetic acid or methyl bromoacetate in the presence of bases such as potassium hydroxide or sodium hydroxide, or with methanesulfonyl halides such as methanesulfonyl chloride in the presence of bases such as triethylamine or diethylaniline, followed by, if necessary and desired, hydrolysis by conventional method, to obtain corresponding products, namely 1-acyl-2,3-dihydro-4(1H)-quinolinone-4-oxime-O-sulfonic acid derivatives, monomethyl ester derivatives of 1-acyl-2,3-dihydro-4(1H)-quinolinone-4-oxime-O-phosphate, 1-acyl-2,3-dihydro-4(1H)-quinolinone-4-oxime-O-acetic acid derivatives and 1-acyl-2,3-di-hydro-4(1H)-quinolinone-4-oxime-O-methanesulfonyl derivatives, respectively.

The above mentioned intermediate compounds, 1-acyl-2,3-dihydro-4(1H)-quinolinone derivatives, may also be reacted with hydroxylamine-O-sulfonic acid in organic solvents such as methanol, ethanol, tetrahydrofuran or dimethylformamide in the presence of pyridine, N,N-dimethylaniline, potassium acetate, sodium carbonate or potassium carbonate to obtain 1-acyl-2,3-dihydro-4(1H)-quinolinone-4-oxime-O-sulfonic acid derivatives.

To demonstrate the utility of the compounds of the present invention, data on diuretic, antihypertensive and antioedematous activities as well as the activity to remove ascites of representative compounds are shown below.

TABLE 1

| Compound number | 1 | 2 | 3 | 4 | 5 | 6 | 7 | 8 | 9 | 10 | 11 | 12 | 13 |
|---|---|---|---|---|---|---|---|---|---|---|---|---|---|
| $R^1$ | t-butyl | ethyl | ethyl | t-butyl | t-butyl | 2-methyl phenyl | 2,4-di-chloro phenyl | 2,4-di-chloro phenyl | 4-chloro phenyl | 4-chloro phenyl | 2,4-di-chloro phenyl | 2-chloro-4-nitro phenyl | 2-bromo phenyl |
| $R^2$ | H | H | H | H | H | H | H | H | H | H | H | H | H |
| $R^3$ | H | H | H | H | H | H | H | $CH_3$ | H | H | H | H | H |
| $R^4$ | $SO_3H$ | $SO_3H$ | $SO_3H$ | $SO_3H$ | $SO_3H$ | $SO_3H$ | $SO_3H$ | $SO_3H$ | $SO_3H$ | $SO_3H$ | $SO_3H$ | $SO_3H$ | $SO_3H$ |
| $R^5$ | 5-Cl | 6-Cl | H | H | H | H | H | 6-Cl | 6-Cl | H | H | H | H |
| $R^6$ | H | H | 7-Cl | 7-Cl | 8-Cl | 7-Cl | 7-F | H | H | 7-Cl | 7-Cl | 7-Cl | 7-Cl |

| Compound number | 14 | 15 | 16 | 17 | 18 | 19 | 20 | 21 | 22 | 23 | 24 |
|---|---|---|---|---|---|---|---|---|---|---|---|
| $R^1$ | ethyl | ethyl | t-butyl | 2,4-di-chloro-phenyl | 2-methyl-phenyl | phenyl | 2-methyl-phenyl | 2-methyl-4-chloro-phenyl | 2,6-di-fluoro-phenyl | 2,3-di-methoxy-phenyl | 2-ethyl-phenyl |
| $R^2$ | H | H | $CH_3$ | H | H | H | H | H | H | H | H |
| $R^3$ | H | H | H | H | H | H | H | H | H | H | H |
| $R^4$ | $CH_2COOH$ | $PO(OH)OCH_3$ | $SO_3H$ | $SO_3H$ | $SO_3H$ | $SO_3H$ | $SO_3H$ | $SO_3H$ | $SO_3H$ | $SO_3H$ | $SO_3H$ |
| $R^5$ | 6-Cl | 6-Cl | 6-Cl | 6-Cl | 6-F | 6-F | 6-$CH_3$ | H | H | H | H |
| $R^6$ | H | H | H | 7-Cl | 7-Cl | 7-Cl | 7-Cl | 7-Cl | 7-Cl | 7-Cl | 7-Cl |

With regard to $R^4$, free acid forms are listed in the table given above, but these compounds may also be isolated as salts of corresponding acids.

EXPERIMENTAL EXAMPLE 1

Diuretic Activity in Dogs

Mongrel dogs weighing 7 to 15 kg were fasted overnight. The animals were restrained in a supine position under pentobarbital anesthesia (30 mg/kg body weight, i.v.), and physiological saline solution was continuously infused into femoral vein via catheter at the rate of 0.15 ml/kg/min. The animals were then laparotomized and left urethra was cannulated to collect urine in 10-minute periods. Compounds to be tested were administered intravenously and the changes in urine output was recorded. Percent increase in urine output was calculated by the formula given below:

Increase in urine output = (Urine output in the 90 minute period after the administration of the compound) − [(Urine output in the 30-minute period before administration) × 3]

Percent increase in urine output = (Increase in urine output by the tested compound) ÷ (Increase in urine output by furosemide) × 100

The results are shown below:

TABLE 2

| Compound | Dose (μg/kg) | Percent increase in urine output |
|---|---|---|
| Furosemide | 100 | 100 |
| 2 | 100 | 31 |
| 3 | 100 | 45 |
| 4 | 100 | 84 |
| 6 | 100 | 355 |
| 7 | 100 | 326 |
| 9 | 100 | 58 |
| 10 | 100 | 249 |
| 11 | 100 | 518 |
| 13 | 100 | 400 |
| 18 | 100 | 331 |
| 19 | 100 | 414 |
| 21 | 100 | 389 |
| 23 | 100 | 374 |
| 24 | 100 | 210 |

All of the tested compounds showed a significant diuretic activity.

EXPERIMENTAL EXAMPLE 2

Suppressive Effect on Carrageenin-Induced Paw Oedema in Rats

Compound to be tested or phenylbutazone was orally administered to groups of Wistar rats (weighing ca. 120 g), each group consisting of 3 to 5 animals. One hour after the administration, 0.1 ml of physiological saline solution containing 1% of carrageenan was subcutaneously injected to the left hind paw. The volume of each paw was measured before and 3 hours after the injection of carrageenan, and the change in the volume was divided by the volume before injection to calculate oedema index. The dose at which oedema is suppressed by 30%, $ED_{30}$, was calculated for each compound.

The results are shown below.

TABLE 3

| Compound | $ED_{30}$ (mg/kg) |
|---|---|
| Phenylbutazone | 68 |
| 2 | 105 |
| 3 | 110 |
| 4 | 67 |
| 7 | 11 |
| 10 | 16 |

All of the tested compounds showed a significant anti-oedematous effect.

EXPERIMENTAL EXAMPLE 3

Hypotensive Action in Spontaneously Hypertensive Rats

Compound to be tested was orally administered to groups of male spontaneously hypertensive rats (SHRs, weighing 250 to 300 g), each group consisting of 3 to 5 animals, once a day for 7 consecutive days. Mean blood pressure of SHRs ranged from 170 to 190 mmHg. Blood pressure was measured before and after the administration with a plethysmograph.

The results are shown below.

TABLE 4

| Compound | Dose (mg/kg) | Blood pressure Before | Blood pressure After |
|---|---|---|---|
| Control | — | 184 | 182 |
| 2 | 100 | 180 | 168 |
| 4 | 100 | 183 | 164 |
| 9 | 100 | 183 | 161 |
| 10 | 30 | 178 | 156 |
| 12 | 100 | 181 | 158 |

Significant hypotensive activity was observed for all of tested compounds.

EXPERIMENTAL EXAMPLE 4

Removal of Ascites from Tumor-Bearing Mice

Two days after intraperitoneal transplantation of $10^6$ cells/animal of P388 murine leukemia cells to 6-to 7-week old $BDF_1$ mice, compounds to be tested were intravenously administered to groups of the tumor-bearing mice, each group consisting of 6 animals. Five hours after the administration, the volume of ascites was measured. The ratio of removal was calculated for each compound on the relative volume of ascites.

The results are shown below.

TABLE 5

| Compound | Dose (mg/kg) | Ratio of removal of ascites (%) |
|---|---|---|
| Control | — | 0 |
| Furosemide | 100 | 19 |
| 2 | 100 | 24 |
| 3 | 10 | 32 |
| 10 | 10 | 35 |
| 11 | 0.1 | 23 |
| 11 | 1 | 37 |

All of the compounds tested showed significant activity, more potent than furosemide, to remove ascites in tumor-bearing mice.

EXPERIMENTAL EXAMPLE 5

Acute Toxicity

Compounds to be tested were intraperitoneally administered to groups of ICR mice weighing about 20 g. Each group consisted of 5 animals. Seven days after the administration, mortality was determined. The results are shown below.

TABLE 6

| Compound | Dose (mg/kg) | Mortality |
|---|---|---|
| 1 | 500 | 0/5 |
| 2 | 500 | 0/5 |
| 3 | 500 | 0/5 |

TABLE 6-continued

| Compound | Dose (mg/kg) | Mortality |
| --- | --- | --- |
| 4 | 500 | 0/5 |
| 5 | 500 | 0/5 |
| 6 | 200 | 0/5 |
| 7 | 200 | 0/5 |
| 8 | 500 | 0/5 |
| 9 | 500 | 0/5 |
| 10 | 200 | 0/5 |
| 11 | 200 | 0/5 |
| 12 | 500 | 0/5 |
| 13 | 200 | 0/5 |

The doses of the experiment described above are considerably higher than that required for their pharmacological activity. Therefore, these compounds were deemed to have large margins for safety.

As demonstrated by the experimental examples described above, these compounds of the present invention possess a potent diuretic activity that can be used for treating and/or preventing hypertension, oedema and/or for removing ascites, and also a large margin for safety within the dose ranges to show these pharmacological activities. Therefore, these compounds are of great use in the treatment of oedema caused by functional insufficiency of heart, kidney or liver, hypertension and accumulation of cancerous ascites.

The 1-acyl-2,3-dihydro-4(1H)-quinolinone-4-oxime derivatives of the present invention represented by the general formula (I) may form pharmaceutically acceptable salts with organic or inorganic bases. Typical examples of such salts of the compounds represented by the general formula (I) include pharmacologically acceptable salts such as alkali metal salts such as sodium salts, potassium salts, etc.; alkaline earth metal salts such as calcium salts, etc.; salts of organic bases such as ammonium salts, benzylamine salts, diethylamine salts, etc.; salts of amino acids such as arginine salts, lysine salts, etc.

The 1-acyl-2,3-dihydro-4(1H)-quinolinone-4-oxime derivatives provided by the present invention can be employed as pharmaceutical compositions, for example, in the form of pharmaceutical compositions containing the 1-acyl-2,3-dihydro-4(1H)-quinolinone-4-oxime derivatives together with appropriate, pharmaceutically acceptable carriers. The pharmaceutical composition may take a solid form, for example, tablets, granules, powders and capsules, or a liquid form, for example, aqueous solutions for injection or suspensions for injection prepared with suspending excipients such as Tween 80 or arabic gum. The compositions may be administered orally or intravenously, but can also be administered subcutaneously, intradermally or intramuscularly. Further, the composition may be formulated for the administration by inhalation, for example as aerosol, for topical application as ointment, or as suppositories. While dose varies depending upon age and conditions of the patient, conditions and kind of diseases, etc., from about 1 to about 5000 mg, preferably from about 10 to about 1000 mg, can be used as a daily dose for an adult. Hereafter the present invention will be described with reference to the examples below but is not deemed to be limited thereof.

EXAMPLE 1

Preparation of 7-chloro-2,3-dihydro-1-(2-methylbenzoyl)-4(1H)-quinolinone

To a mixture of 7-chloro-2,3-dihydro-4(1H)-quinolinone (20.0 g), pyridine (26 g) and dichloromethane (200 ml) was added dropwise 2-methylbenzoyl chloride (26 g) at room temperature with stirring. The mixture was stirred under reflux for 4 hours. The reaction mixture was poured into 500 ml of water, then shaken with additional dichloromethane (1000 ml). The organic layer was washed once with 1 N HCl (100 ml), twice with water (200 ml each) and once with saturated aqueous NaCl solution, then dried over anhydrous sodium sulfate. Solvent was removed in vacuo and the residue was recrystallized to obtain 7-chloro-2,3-dihydro-1-(2-methylbenzoyl)-4(1H)-quinolinone (yield 28 g) as white crystal.

Melting point: 106.5°-108.1° C.

IR (KBr, cm$^{-1}$): 1695, 1655, 1405, 1380.

NMR (CDCl$_3$, ppm): 2.34 (3H, s), 2.80 (2H, t), 4.16 (2H, t), 7.00-8.00 (7H, m, aromatic).

EXAMPLE 2

Preparation of 6-chloro-1-(2,4-dichlorobenzoyl)-2,3-dihydro-4(1H)-quinolinone

To a mixture of 6-chloro-2,3-dihydro-4(1H)-quinolinone (20 g), pyridine (26 g) and dioxane (200 ml) was added 2,4-dichlorobenzoylchloride (30 g) dropwise under cooling at 0° C. to 5° C. with stirring. The mixture was allowed to react at room temperature for additional 3 hours. The reaction mixture was poured into 500 ml of water, then shaken with dichloromethane (1000 ml). The organic layer was washed once with 1 N HCl (100 ml), twice with water (200 ml each) then once with saturated aqueous NaCl solution (200 ml) and dried over anhydrous sodium sulfate. Dichloromethane was removed in vacuo and the residue was recrystallized with dichloromethane and n-hexane to obtain 6-chloro-1-(2,4-dichlorobenzoyl)-2,3-dihydro-4(1H)-quinolinone (yield 35 g) as white crystal.

Melting point: 176.8°-177.8° C.

IR (KBr, cm$^{-1}$): 1700, 1670, 1480, 1390.

NMR (CDCl$_3$, ppm): 2.87 2H, t , 4.22 2H, t), 7.07-8.04 (6H, m, aromatic).

EXAMPLE 3

Preparation of 8-chloro-1-(2,4-dichlorobenzoyl)-2,3-dihydro-4(1H)-quinolinone

To a mixture of 8-chloro-2,3-dihydro-4(1H)-quinolinone (30 g), pyridine (52 g) and dioxane (400 ml) was added 2,4-dichlorobenzoylchloride (100 g) dropwise at room temperature with stirring. The mixture was then heated under reflux for 5 hours. After cooling, the reaction mixture was subjected to the procedure described in example 2, and 61 g of 8-chloro-1-(2,4-dichlorobenzoyl)-4-[(2,4-dichlorobenzoyl)oxy]-1,2-dihydroquinoline was obtained. All of the product was then dissolved in ethanol (400 ml) and 4.5 g of NaOH was slowly added to the solution over a 30-minute period with stirring, maintaining the temperature at 0° C. to 5° C. Stirring was continued at room temperature for 1 hour. The reaction mixture was poured into 1000 ml of water, then shaken with 2000 ml of dichloromethane. The organic layer was washed twice with water (300 ml each) then once with saturated aqueous NaCl solution (300 ml) and dried over anhydrous sodium sulfate. Dichloromethane was removed in vacuo and the residue was recrystallized with dichloromethane and n-hexane to obtain 8-chloro-1-(2,4-dichlorobenzoyl)-2,3-dihydro-4(1H)-quinolinone (yield 32 g) as white crystal.

Melting point: 157.0°-159.4° C.

IR (KBr, cm⁻¹): 1700, 1680, 1440, 1280.

NMR (CDCl₃, ppm): 2.73 (2H, t), 3.97 (2H, t), 6.73-7.84 (6H, m).

EXAMPLE 4

Preparation of 6-chloro-1-(2,4-dichlorobenzoyl)-2,3-dihydro-3-methyl-4(1H)-quinolinone To a cooled (−20° C. to −15° C.) solution of diisopropylamine (4.7 g) in anhydrous tetrahydrofuran (100 ml) was added dropwise n-hexane solution (29 ml) of 1.6 N butyl lithium over a 30-minute period in a nitrogen atmosphere, and stirring was continued for 30 minutes after the mixed solution was returned to 0° C. Then the solution was cooled to −75° C. with acetone-dry ice and 15 g of 6-chloro-1-(2,4-dichlorobenzoyl)-2,3-dihydro-4(1H)-quinolinone dissolved in 150 ml of anhydrous tetrahydrofuran was added dropwise over a 1-hour period. The reaction mixture was stirred for another 1 hour at −75° C., and methyl iodide (18 g) was added dropwise with stirring over a 30-minute period. The reaction mixture was then slowly warmed to 0° C. over two hour, and acidified under cooling with 2 N hydrochloric acid to be weakly acidic. The reaction mixture was poured into 300 ml of water, then shaken with ethyl acetate (500 ml). The organic layer was washed once with saturated aqueous NaCl solution (200 ml) and dried over anhydrous sodium sulfate. Ethyl acetate was removed in vacuo and the residue was subjected to silica gel column chromatography using a hexane-ethyl acetate mixture (4:1) to obtain 6-chloro-1-(2,4-dichlorobenzoyl)-2,3-dihydro-3-methyl-4(1H)-quinolinone (yield 7.8 g) as white crystal.

Melting point: 156.7°-159.4° C.

IR (KBr, cm⁻¹): 1690, 1650, 1470, 1385.

NMR (CDCl₃, ppm): 1.35 (3H, d), 3.61 (1H, m), 4.38 (2H, d), 6.89 - 7.95 (6H, m).

EXAMPLE 5

Preparation of 7-chloro-1-(2,4-dichlorobenzoyl)-2,3-dihydro-4(1H)-quinolinone

To a mixture of 7-chloro-2,3-dihydro-4(1H)-quinolinone (25 g), pyridine (32 g) and dioxane (200 ml) was added 2,4-dichlorobenzoylchloride (37 g) dropwise under cooling at 0° C. to 5° C. with stirring. The mixture was allowed to react at room temperature for additional 3 hours. The reaction mixture was subjected to the procedure described in example 2, and 43 g of 7-chloro-1-(2,4-dichlorobenzoyl)-2,3-dihydro-4-(1H)-quinolinone was obtained as white crystal.

Melting point: 159.0°-162.9° C.

IR (KBr, cm⁻¹): 1695, 1660, 1395, 1195.

NMR (CDCl₃, ppm): 2.78 2H, t), 4.08 (2H, t), 7.03-7.95 (6H, m, aromatic).

EXAMPLE 6

Preparation of 7-chloro-2,3-dihydro 1-(2-methylbenzoyl)-4(1H)-quinolinone-4-oxime-O-sulfonic acid potassium salt (Compound 6)

To a mixture of 7-chloro-2,3-dihydro-1-(2-methylbenzoyl)-4(1H)-quinolinone (10.0 g) obtained in example 1, methanol (150 ml) and dichloromethane (100 ml) was added hydroxylamine-0-sulfonic acid (11 g) at room temperature with stirring. The mixture was stirred at room temperature for 30 minutes, and aqueous solution of potassium carbonate (14 g in 20 ml of water) was added at once. The reaction mixture was stirred at room temperature for 2 hours, and the solvent was removed in vacuo. The residue was subjected to silica gel column chromatography using dichloromethane-methanol mixture (5:1) and recrystallized with a mixed solvent of methanol-carbon tetrachloride to obtain 7-chloro-2,3-dihydro-1-(2-methylbenzoyl)-4(1H)-quinolinone-4-oxime-O-sulfonic acid potassium salt (yield 12.0 g) as white crystal.

Melting point: 189.0° C. (decomposition).

IR (KBr, cm⁻¹): 1660, 1380, 1240.

NMR (DMSO-d₆, ppm): 2.22 (3H, s), 2.81 (2H, t), 3.73 (2H, t), 6.90-7.95 (7H, m, aromatic).

EXAMPLE 7

Preparation of 7-chloro-2,3-dihydro-1-(2-methylbenzoyl)-4(1H)-quinolinone-4-oxime-O-sulfonic acid potassium salt (compound 6).

(Step 1)

To a mixture of 7-chloro-2,3-dihydro-1-(2-methylbenzoyl)-4(1H)-quinolinone (14.9 g), obtained in example 1, and ethanol (250 ml) were added hydroxyl amine hydrochloride (7 g) and pyridine (8.5 g), and the mixture was heated under reflux for 1.5 hours. After cooling, the reaction mixture was poured into 1000 ml of water, and precipitated crystals were separated by filtration, washed, dried and recrystallized with ethanol to obtain 7-chloro-2,3-dihydro-1-(2-methylbenzoyl)-4(1H)-quinolinone-4-oxime (yield 13.6 g) as white crystal.

Melting point: 166.0°-168.4° C.

IR (KBr, cm⁻¹): 3330, 1635, 1400.

NMR (DMSO-d₆, ppm): 2.20 (3H, s), 2.81 (2H, t), 3.77 (2H, t), 7.05-7.98 (7H, m, aromatic).

(Step 2)

The product of Step 1 (13.6 g) was dissolved in dichloromethane (250 ml) and sulfur trioxide-pyridine complex (7 g) was added. The reaction mixture was stirred at room temperature for 24 hours and ca. 150 ml of the solvent was removed in vacuo. To the residue was added methanol (200 ml) and then aqueous potassium carbonate solution (6 g in 10 ml of water) at once, and the mixture was subjected to the procedure described in example 6, and 13 g of 7-chloro-2,3-dihydro-1-(2-methylbenzoyl)-4(1H)-quinolinone-4-oxime-O-sulfonic acid potassium salt was obtained as white crystal, of which IR and NMR spectra and melting point were completely in agreement with the product of example 6.

EXAMPLE 8

Preparation of 7-chloro-6-fluoro-2,3-dihydro-1-(2-methylbenzoyl)-4(1H)-quinolinone-4-omine-O-sulfonic acid potassium salt (compound 18)

(Step 1)

Preparation of 7-chloro-6-fluoro-2,3-dihydro-4-(1H)-quinolinone

A mixture of polyphosphoric acid (600 g) and 3-(3-chloro-4-fluorophenylamino)propionic acid (38 g), which was synthesized from 3-chloro-4-fluoroaniline and acrylic acid or methyl acrylate by the method of W. S. Johnson et al. (The Journal of American Chemical Society, volume 71, page 1901, (1949)), was stirred at 110° C. for 70 minutes. The reaction mixture was poured into 1500 ml of water, then shaken with dichloromethane (1500 ml). The organic layer was washed twice with saturated aqueous NaCl solution (200 ml each) and dried over anhydrous sodium sulfate. Dichloromethane was removed in vacuo and the residue was subjected to silica gel column chromatography using a mixed solvent (n-hexane : ether=4:1) to obtain 7-chloro-6-fluoro-2,3-dihydro-4(1H)-quinolinone (yield 20 g) as pale yellow crystal.

Melting point: 192.0°–194.0° C.

IR (KBr, cm$^{-1}$): 3350, 1645, 1250, 1160.

NMR (DMSO-d$_6$+CdCl$_3$, ppm): 2.61 (2H, t), 3.52 (2H, t), 6.83 (1H, d), 7.43 (1H, d).

(Step 2)

Preparation of 7-chloro-6-fluoro-1-(2-methylbenzoyl)-2,3-dihydro-4(1H)-quinolinone The product of Step 1 (15 g), 2-methylbenzoyl chloride (17 g), pyridine (12 g) and dichloromethane (200 ml) were subjected to the reaction and purification procedure described in Example 1, and 7-chloro-6-2,3-dihydro-1-(2-methylbenzoyl)-4(1H)-quinolinone (21 g) was obtained.

Melting point: 84.9°–88.7° C.

IR (KBr, cm$^{-1}$): 1700, 1665, 1480, 1370.

NMR (CDCl$_3$, ppm): 2.38 (3H, s), 2.81 (2H, t), 4.16 (2H, t), 7.16–7.78 (6H, m).

(Step 3)

Preparation of 1-(2-methylbenzoyl-7-chloro-6-fluoro-2,3-dihydro-4(1H)-quinolinone-4-oxime-O-sulfonic acid potassium salt The product of Step 2 (10 g, hydroxylamine-O-sulfuric acid (3.6 g), potassium carbonate (4.4 g) and methanol (100 ml) were subjected to the reaction and purification process described in Example 6, and 1-(2-methylbenzoyl)-7-chloro-6-fluoro-2,3-dihydro-4-(1H)-quinolinone-4-oxime-O-sulfuric acid potassium salt (4 g) was obtained as white crystal.

Melting point: 204.1° C. (decomposition).

IR (KBr, cm$^{-1}$): 1650, 1375, 1210.

NMR (DMSO-d$_6$, ppm): 2.23 (3H, s), 2.82 (2H, t), 3.75 (2H, t), 7.16–7.79 (6H, m, aromatic).

EXAMPLE 9

Preparation of 7-chloro-1-(2,4-dichlorobenzoyl)-2,3-dihydro-4(1H)-quinolinone-4-oxime-O-sulfonic acid potassium salt (compound 11).

To a mixture of 7-chloro-1-(2,4-dichlorobenzoyl)-2,3-dihydro-4(1H)-quinolinone (14.5 g), obtained in example 5, methanol (200 ml) and dichloromethane (200 ml) was added 4.6 g of hydroxylamine-O-sulfonic acid with stirring at room temperature. After stirring for 30 minutes at room temperature, aqueous solution of potassium carbonate (5.6 g in 10 ml of water) was added to the mixture at once and stirring was continued for another 2 hours. Precipitated crystals were removed by filtration and the solvent was removed in vacuo. The residue was subjected to silica gel column chromatography using a dichloromethane-methanol mixture (10:1), then recrystallized with methanol and carbon tetrachloride to obtain 7-chloro-1-(2,4-dichlorobenzoyl-2,3-dihydro-4(1H)-quinolinone-4-oxime-O-sulfonic acid potassium salt (yield 10.0 g) as white crystal.

Melting point: 217.5° C. (decomposition).

IR (KBr, cm$^{-1}$): 1660, 1395, 1240.

NMR (DMSO-d$_6$, ppm): 2.80 (2H, t), 3.59 (2H, t), 7.12–7.93 (6H, m, aromatic).

EXAMPLE 10

Preparation of 7-chloro-1-(2,4-dichlorobenzoyl)-2,3-dihydro-4(1H)-quinolinone-4-oxime-O-sulfonic acid sodium salt (compound 11).

To a mixture of 7-chloro-1-(2,4-dichlorobenzoyl)-2,3-dihydro-4(1H)-quinolinone (14.5 g), obtained in example 5, methanol (200 ml) and dichloromethane (200 ml) was added 4.6 g of hydroxylamine-O-sulfonic acid with stirring at room temperature. After stirring for 30 minutes at room temperature, aqueous solution of sodium carbonate (4.3 g in 10 ml of water) was added to the mixture at once and stirring was continued for another 2 hours. Precipitated crystals were removed by filtration and the solvent was removed in vacuo. The residue was subjected to silica gel column chromatography using a dichloromethane-methanol mixture (10 l), then recrystallized with methanol and carbon tetrachloride to obtain 7-chloro-1-(2,4-dichlorobenzoyl)-2,3-dihydro-4(1H)-quinolinone-4-oxime-O-sulfonic acid sodium salt (yield 8.0 g) as white crystal.

Melting point: 176.5° C. (decomposition).

IR (KBr, cm$^{-1}$): 1670, 1395, 1235.

NMR (DMSO-d$_6$, ppm): 3.05 (2H, t), 3.90 (2H, t), 7.25–8.15 (6H, m, aromatic).

EXAMPLE 11

Preparation of 7-chloro-1-(2,4-dichlorobenzoyl)-2,3-dihydro-4(1H)-quinolinone-4-oxime-O-sulfonic acid potassium salt (compound 11)

(Step 1)

To a mixture of 7-chloro-1-(2,4-dichlorobenzoyl)-2,3-dihydro-4(1H)-quinolinone (17.5 g), obtained in example 5, and ethanol (250 ml) were added hydroxyl amine hydrochloride (7 g) and pyridine (8.5 g), and the mixture was heated under reflux for 1.5 hours. After cooling, the reaction mixture was poured into 1000 ml of water, and precipitated crystals were separated by filtration, washed, dried and recrystallized with ethanol to obtain 7-chloro-1-(2,4-dichlorobenzoyl)-2,3-dihydro-4(1H)-quinolinone-4-oxime (yield 16 g) as white crystal.

Melting point: 230.7°–232.3° C.

IR (KBr, cm$^{-1}$): 3250, 1635, 1420, 945.

NMR (DMSO-d$_6$, ppm): 2.72 (2H, t), 3.57 (2H, t), 7.05–7.94 (6H, m, aromatic).

(Step 2)

The product of Step 1 (16 g) was dissolved in dichloromethane (250 ml) and sulfur trioxide-pyridine complex (7 g) was added. The reaction mixture was stirred at room temperature for 24 hours and the solvent was removed in vacuo. To the residue was added methanol (200 ml) and then aqueous potassium carbonate solution (6 g in 10 ml of water) at once, and the mixture was subjected to the procedure described in example 9, and 13 g of 7-chloro-1-(2,4-dichlorobenzoyl)-2,3-dihydro-4(1H)-quinolinone-4-oxime-O-sulfonic acid potassium salt was obtained as white crystal, of which IR and NMR spectra and melting point were completely in agreement with the product of example 9.

EXAMPLE 12

Preparation of 6-chloro-2,3-dihydro-1-(1-oxopropyl)-4(1H)-quinolinone-4-oxime-O-acetic acid (compound 14)

To a mixture of bromoacetic acid (7.7 g), potassium hydroxide (6.5 g) and water (60 ml) was added 6-chloro-2,3-dihydro-1-(1-oxopropyl)-4(1H)-quinolinone-4-oxime (12.7 g) slowly under cooling in an ice bath. The mixture was stirred for 24 hours at room temperature, then acidified with 2 N HCl to pH 3.0 in an ice bath. The acidified mixture was poured into 150 ml of water, then shaken with ethyl acetate (500 ml). The organic layer was washed once with saturated aqueous NaCl solution (500 ml) and dried over anhydrous sodium sulfate. Solvent was removed in vacuo and the residue was subjected to silica gel column chromatography using a dichloromethane-methanol mixture (9 : 1) to obtain 6-chloro-2,3-dihydro-1-(1-oxopropyl)-4(1H)-quinolinone-4-oxime-O-acetic acid (yield 10.5 g) as white crystal.

Melting point: 142.8°-144.0° C.

IR (KBr, cm$^{-1}$): 3300-2800, 1740, 1650, 1480, 1390.

NMR (DMSO-d$_6$, ppm): 1.03 (3H, t), 2.52 (2H, q), 2.84 (2H, t), 3.79 (2H, t), 4.69 (2H, s), 7.26-7.75 (3H, m, aromatic).

EXAMPLE 13

Preparation of 6-chloro-2,3-dihydro-1-(1-oxopropyl)-4(1H)-quinolinone-4-oxime-O-phosphoric acid monomethyl ester (compound 15)

To a cold (-75° C.) solution of 6-chloro-2,3-di-hydro-1-(1-oxopropyl)-4(1H)-quinolinone-4-oxime (7.5 g) in anhydrous tetrahydrofuran (150 ml) was added dropwise n-hexane solution (21 ml) of 1.6 N butyl lithium over a 30-minute period in a nitrogen atmosphere, and stirring was continued for 30 minutes at −75° C. To the mixture, methyl dichlorophosphate (4.9 g) was added dropwise over a 30-minute period at −75° C., and stirring was continued for 30 minutes at −70° C. to −60° C. for 2 hours. The reaction mixture was slowly warmed to about 0° C. and acidified with 1 N HCl to pH 2.0. The acidified mixture was stirred for 5 hours at room temperature, then poured into 200 ml of water and shaken with ethyl acetate (500 ml). The organic layer was washed once with saturated aqueous NaCl solution (200 ml) and dried over anhydrous sodium sulfate. Ethyl acetate was removed in vacuo and the residue was subjected to silica gel column chromatography using a dichloromethane-methanol mixture (19:1) to obtain 6-chloro-2,3-dihydro-1-(1-oxopropyl)-4(1H)quinolinone-4-oxime-0-phosphoric acid monomethyl ester (yield 7.2 g) as white crystal.

Melting point: 71.0°-75.0° C.

IR (KBr, cm$^{-1}$): 3420, 2950, 1680, 1395, 1195.

NMR (DMSO-d$_6$, ppm): 1.01 (3H, t), 2H, q), 2.88 (2H, t), 3.62 (3H, d), 3.78 (2H, t), 7.22-7.85 (3H, m, aromatic).

EXAMPLE 14

Preparation of 6-chloro-1-(2,4-dichlorobenzoyl)-2,3-dihydro-4(1H)-quinolinone-4-oxime mesylate To a mixture of 6-chloro-1-(2,4-dichlorobenzo-yl)-2,3-dihydro-4(1H)-quinolinone-4-oxime (10.0 g), triethylamine (4.1 g) and dichloromethane (150 ml) was added dropwise methanesulfonyl chloride (3.5 g) at −20° C. with stirring. The mixture was stirred at −20° C. for 30 minutes and dichloromethane (300 ml) was added. The reaction mixture was sequentially washed with 1 N HCl, saturated aqueous sodium bicarbonate solution, then with saturated aqueous NaCl solution and dried over anhydrous sodium sulfate. Solvent was removed in vacuo and the residue was recrystallized with ether and n-hexane to obtain 6-chloro-1-(2,4-dichlorobenzoyl)-2,3-dihydro-4(1H)-quinolinone-4-oxime mesylate (yield 11 g) as white crystal.

Melting point: 197.4°-198.1° C.

IR (KBr, cm$^{-1}$): 1660, 1365, 1180.

NMR (DMSO-d$_6$, ppm): 3.03 (2H, t), 3.38 (3H, s), 3.72 (2H, t), 7.12-7.92 (6H, m, aromatic).

Compounds of examples 15 to 266 are summarized to the following Tables 8 to 18 together with corresponding IR and NMR data (NMR data were generally measured at 90 MHz except several data, which were measured at 60 MHz and marked with asterisks(*)) and melting or decomposition points. The methods by which these compounds are synthesized can be classified into three groups as shown below.

TABLE 7

| Group | Synthetic method (representative example number) | Example number in Tables 8 to 18 |
|---|---|---|
| A | 1 | 27-59, 64-144 |
| B | 3 | 60-63 |
| C | 6 | 145-208, 210-215, 218, 220-266 |
| D | 7 | 209, 216, 217, 219 |
| E | 8 (Step 1) | 15-26 |

TABLE 8

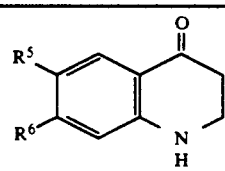

| Ex. No. | R$^5$ | R$^6$ | IR(KBr, cm$^{-1}$) | NMR(CDCl$_3$, ppm) | M.P.(°C.) |
|---|---|---|---|---|---|
| 15 | H | —SCH$_3$ | 3350, 1640, 1240, 1180 | 2.42(3H, s), 2.62 (2H, t), 3.51(2H, dt), 4.53(1H, m), 6.35-6.58(2H, m), 7.60-7.73(1H, m) | 133.9~137.3 |
| 16 | H | —NO$_2$ | 3350, 1670, 1355, 1190 | [DMSO-d$_6$+CDCl$_3$] 2.61(2H, t), 3.53, (2H, dt), 7.00(1H, m), 7.07-7.79 (3H, m) | 229.0~232.7 |

TABLE 8-continued

| Ex. No. | R⁵ | R⁶ | IR(KBr, cm⁻¹) | NMR(CDCl₃, ppm) | M.P.(°C.) |
|---|---|---|---|---|---|
| 17 | H | Br | 3370, 1660, 1240, 1180 | 2.64(2H, t), 3.53 (2H, dt), 4.42(1H, m), 6.67–6.82(2H, m), 7.51–7.65(1H, m) | 139.6~141.1 |
| 18 | H | F | 3300, 1620, 1255, 1195 | 2.62(2H, t), 3.53 (2H, dt), 4.51(1H, m), 6.19–6.50(2H, m), 7.73–7.97(1H, m) | 101.6~102.5 |
| 19 | H | I | 3360, 1650, 1240, 1180 | 2.63(2H, t), 3.52 (2H, dt), 4.32(1H, m), 6.90–7.04(2H, m), 7.36–7.47(1H, m) | 142.4~148.0 |
| 20 | H | —CF₃ | 3370, 1660, 1240, 1160 | 2.71(2H, t), 3.60 (2H, dt), 4.58(1H, m), 6.75–6.95(2H, m), 7.78–7.96(1H, m) | 163.8~165.0 |
| 21 | H | —COCH₃ | 3370, 1700, 1230, 1180 | 2.58(3H, s), 2.74 (2H, t), 3.63(2H, dt), 4.64(1H, m), 7.21–7.30(2H, m), 7.82–7.98(1H, m) | 162.2~167.2 |
| 22 | H | —COOCH₃ | 3350, 1725, 1240, 1170 | 2.82(2H, t), 3.63 (2H, dt), 3.91(3H, s), 4.56(1H, m), 7.23–7.98(3H, m) | 142.1~146.8 |
| 23 | F | F | 3360, 1640, 1260, 1160 | 2.75(2H, t), 3.53 (2H, dt), 4.29(1H, m), 6.20–6.41(1H, m), 7.36–7.53(1H, m) | 155.4~156.6 |
| 24 | Cl | F | 3350, 1660, 1240, 1160 | 2.77(2H, t), 3.71 (2H, dt), 4.71(1H, m), 6.50–6.67(1H, d), 7.96–8.11(1H, d) | 171.3~176.3 |
| 25 | Br | Cl | 3350, 1660, 1230, 1155 | [DMSO-d₆] 2.53(2H, t), 3.47 (2H, t), 7.04(1H, s), 7.82(1H, s) | 175.7~180.9 |
| 26 | —OCH₃ | —OCH₃ | 3350, 1660, 1265, 1170 | 2.64(2H, t), 3.55 (2H, dt), 3.82(3H, s), 3.86(3H, s), 4.30(1H, m), 6.12 (1H, s), 7.29(1H, s) | 105.1~108.9 |

TABLE 9

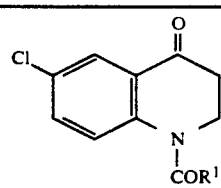

| Ex. No. | R¹ | IR(KBr, cm⁻¹) | NMR(CDCl₃, ppm) | M.P. (°C.) |
|---|---|---|---|---|
| 27 | —OCH₃ | 1730, 1695, 1490, 1225 | 2.77(2H, t), 3.88(3H, s), 4.20(2H, t), 7.39–8.00(3H, m) | 106.7~107.1 |
| 28 | —CH₃ | 1700, 1670, 1480, 1200 | 2.33(3H, s), 2.79(2H, t), 4.20(2H, t), 7.47–7.98(3H, m) | 149.2~150.2 |
| 29 | —CH₂CH₃ | 1700, 1670, 1480, 1185 | 1.23(3H, t), 2.58(2H, q), 2.76(2H, t), 4.18(2H, t), 7.45–7.98(3H, m) | 105.5~106.4 |
| 30 | —(CH₂)₃CH₃ | 1680, 1470, 1380, 1180 | 0.91(3H, t), 1.13–1.86 (4H, m), 2.54(2H, t), 2.75 (2H, t), 4.14(2H, t), 7.38–7.91(3H, m) | 71.3~74.2 |
| 31 | —(CH₂)₇(CH₃) | 1690, 1670, 1460, 1170 | 0.87(3H, t), 1.07–2.24 (12H, m), 2.57(2H, t), | (Oil) |

TABLE 9-continued
| Ex. No. | R¹ | IR(KBr, cm⁻¹) | NMR(CDCl₃, ppm) | M.P. (°C.) |
|---|---|---|---|---|
| | | | 2.78(2H, t), 4.20(2H, t), 7.48-8.00(3H, m) | |
| 32 | —(CH₂CH(CH₃)₂ | 1700, 1655, 1485, 1185 | 0.98(6H, d), 2.18(1H, m), 2.46(2H, d), 2.78(2H, t), 4.21(2H, t), 7.44-8.02 (3H, m) | 65.3~74.5 |
| 33 | —C(CH₃)₃ | 1695, 1650, 1470, 1160 | 1.41(9H, s), 2.73(2H, t) 4.15(2H, t), 7.16-7.88(3H, m) | 163.1~164.3 |
| 34 | —CH₂CH₂Cl | 1700, 1670, 1390, 1190 | 2.80(2H, t), 3.04(2H, t), 3.88(2H, t), 4.23(2H, t), 7.42-7.99(3H, m) | 107.0~117.1 |
| 35 | —C(CH₃)₂CH₂Cl | 1700, 1660, 1475, 1150 | 1.49(6H, s), 2.78(2H, t), 3.71(2H, s), 4.15(2H, t), 7.37-7.92(3H, m) | 148.0~150.9 |
| 36 | —CH₂CH₂CO₂CH₃ | 1740, 1655, 1480, 1170 | 2.72(2H, t), 2.75(2H, t), 2.79(2H, t), 3.66(3H, s), 4.19(2H, t), 7.18-7.93 (3H, m) | 107.8~108.4 |
| 37 | —CH₂OCH₃ | 1690, 1475, 1305, 1200 | 2.81(2H, t), 3.47(3H, s), 4.18(2H, t), 4.27(2H, s), 7.41-8.02(3H, m) | 96.5~97.5 |
| 38 |  | 1700, 1660, 1490, 1180 | 0.78-1.33(4H, m), 1.80-2.11(1H, m), 2.77(2H, t), 4.24(2H, t), 7.17-7.95 (3H, m) | 146.7~148.9 |
| 39 | 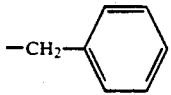 | 1700, 1680, 1470, 1190 | 1.00-1.96(11H, m), 2.73 (2H, t), 4.15(2H, t), 7.38-7.96(3H, m) | 92.7~94.0 |
| 40 | 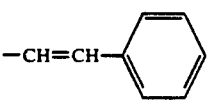 | 1700, 1680, 1480, 1195 | 2.53(2H, t), 3.90(2H, s), 4.08(2H, t), 7.10-7.83(8H, m) | 102.7~104.9 |
| 41 | 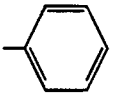 | 1690, 1655, 1470, 1180 | 2.79(2H, t), 4.30(2H, t), 6.73(1H, d), 7.11-7.88 (8H, m), 7.71(1H, d) | 163.1~164.4 |
| 42 | 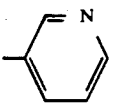 | 1695, 1665, 1375, 1190 | 2.82(2H, t), 4.25(2H, t), 6.81-7.95(8H, m) | 135.9~137.2 |
| 43 | 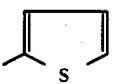 | 1700, 1655, 1485, 1370 | 2.88(2H, t), 4.29(2H, t), 6.78-7.37(3H, m), 7.67-8.66(4H, m) | 161.8~162.6 |
| 44 |  | 1695, 1665, 1365, 1240 | 2.82(2H, t), 4.29(2H, t), 6.82-7.91(6H, m) | 147.7~148.7 |

TABLE 9-continued
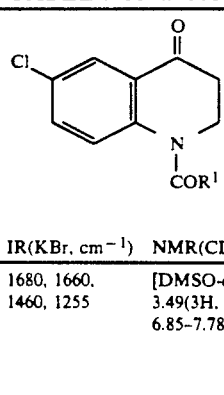
| Ex. No. | R[1] | IR(KBr, cm[-1]) | NMR(CDCl$_3$, ppm) | M.P. (°C.) |
|---|---|---|---|---|
| 45 | 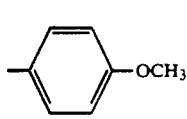 | 1680, 1660, 1460, 1255 | [DMSO-d$_6$] 2.78(2H, t), 3.49(3H, s), 4.11(2H, t), 6.85-7.78(7H, m) | 138.1~139.1 |
| 46 | 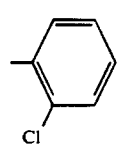 | 1700, 1680, 1365, 1260 | 2.81(2H, t), 3.80(3H, s), 4.23(2H, t), 6.71-7.97(7H, m) | 152.5~156.4 |
| 47 | 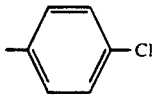 | 1695, 1660, 1475, 1380 | 2.82(2H, t), 4.16(2H, t), 7.02-7.93(7H, m) | 122.2~123.4 |
| 48 | 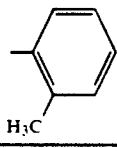 | 1690, 1665, 1360, 1190 | 2.28(2H, t), 4.23(2H, t), 6.72-7.89(7H, m) | 170.8~171.9 |
| 49 | 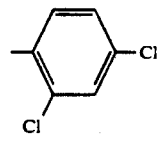 | 1695, 1650, 1480, 1385 | 2.32(3H, s), 2.81(2H, t), 4.19(2H, t), 7.01-8.00(7H, m) | 89.1~92.6 |
TABLE 10
| Ex. No. | R[1] | R[5] | IR(KBr, cm[-1]) | NMR(CDCl$_3$, ppm) | M.P. (°C.) |
|---|---|---|---|---|---|
| 50 | —CH$_2$CH$_3$ | Br | 1695, 1645, 1480, 1180 | 1.21(3H, t), 2.57(2H, q), 2.73(2H, t), 4.15(2H, t), 7.17-8.10(3H, m) | 103.6~107.8 |
| 51 | (3,4-dichlorophenyl) | F | 1690, 1645, 1490, 1390 | 2.82(2H, t), 4.12(2H, t), 6.81-7.69(6H, m) | 159.0~159.5 |
| 52 | —CH$_2$CH$_3$ | —OCH$_3$ | 1695, 1650, 1500, 1180 | 1.21(3H, t), 2.55(2H, q), 2.74(2H, t), 3.82(3H, s), 4.18(2H, t), 6.98-7.47 (3H, m) | 105.2~107.3 |
| 53 | —CH$_2$CH$_3$ | H | 1700, 1655, 1490, 1210 | 1.26(3H, t), 2.57(2H, q), 2.74(2H, t), 4.20(2H, t), 7.09-8.04(4H, m) | 50.0~55.0 |

TABLE 10-continued
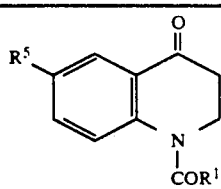
| Ex. No. | R¹ | R⁵ | IR(KBr, cm⁻¹) | NMR(CDCl₃, ppm) | M.P. (°C.) |
|---|---|---|---|---|---|
| 54 |  | H | 1690, 1640, 1480, 1385 | 2.84(2H, t), 4.20(2H, t), 7.04–8.02(7H, m) | 135.2–137.7 |
| 55 |  | H | 1680, 1635, 1480, 1375 | 2.33(3H, s), 2.83(2H, t), 4.23(2H, t), 6.99–8.10(8H, m) | 149.0–150.7 |
TABLE 11
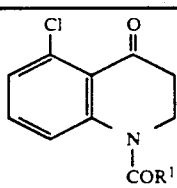
| Ex. No. | R¹ | IR(KBr, cm⁻¹) | NMR(CDCl₃, ppm) | M.P.(°C.) |
|---|---|---|---|---|
| 56 | —CH₂CH₃ | 1700, 1660, 1460, 1190 | 1.18(3H, t), 2.49(2H, q), 2.78(2H, t), 4.10(2H, t), 7.13–7.31(3H, m) | 95.8–98.0 |
| 57 | —C(CH₃)₃ | 1690, 1655, 1450, 1360 | 1.36(9H, s), 2.81(2H, t), 4.15(2H, t), 7.18–7.38(3H, m) | 101.7–103.6 |
| 58 | —C₆H₄Cl (p) | 1700, 1665, 1460, 1375 | 2.91(2H, t), 4.24(2H, t), 6.57–7.53(7H, m) | 143.6–145.2 |
| 59 | o-tolyl | 1680, 1640, 1445, 1360 | 2.31(3H, s), 2.87(2H, t), 4.16(2H, t), 6.91–7.48(7H, m) | 171.7–173.4 |
TABLE 12
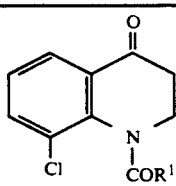
| Ex. No. | R¹ | IR(KBr, cm⁻¹) | NMR(CDCl₃, ppm) | M.P.(°C.) |
|---|---|---|---|---|
| 60 | —CH₂CH₃ | 1700, 1670, 1445, 1180 | 1.13(3H, t), 2.55(2H, q), 2.76(2H, t), 3.64(2H, t), 7.12–7.91(3H, m) | 73.4–74.8 |
| 61 | —C(CH₃)₃ | 1700, 1660, 1440, 1275 | 1.43(9H, s), 2.76(2H, t), 4.18(2H, t), 7.08–7.96(3H, m) | 131.3–132.0 |

TABLE 12-continued

[Structure: 8-chloro-1-(COR¹)-2,3-dihydroquinolin-4(1H)-one]

| Ex. No. | R¹ | IR(KBr, cm⁻¹) | NMR(CDCL₃, ppm) | M.P.(°C.) |
|---|---|---|---|---|
| 62 | [4-chlorophenyl] | 1700, 1675, 1450, 1365 | 2.82(2H, t), 4.20(2H, t), 7.22–8.03(7H, m) | 131.1–134.1 |
| 63 | [2-methylphenyl] | 1700, 1660, 1440, 1360 | 2.51(3H, s), 2.74(2H, t), 4.01(2H, t), 7.08–8.02(7H, m) | 117.4–120.6 |

TABLE 13

[Structure: 7-chloro-1-(COR¹)-2,3-dihydroquinolin-4(1H)-one]

| Ex. No. | R¹ | IR(KBr, cm⁻¹) | NMR(CDCl₃, ppm) | M.P. (°C.) |
|---|---|---|---|---|
| 64 | —CH₂CH₃ | 1700, 1670, 1395, 1205 | 1.23(3H, t), 2.59(2H, q), 2.72(2H, t), 4.13(2H, t), 7.03–7.88(3H, m) | 104.3–109.8 |
| 65 | —C(CH₃)₃ | 1710, 1660, 1360, 1160 | 1.41(9H, s), 2.76(2H, t), 4.16(2H, t), 7.01–7.88(3H, m) | 124.3–128.1 |
| 66 | —C(CH₃)₂CH₂Cl | 1700, 1665, 1360, 1200 | 1.49(6H, s), 2.76(2H, t), 3.72(2H, s), 4.14(2H, t), 7.07–7.91(3H, m) | 108.8–110.8 |
| 67 | [2-chlorophenyl] | 1715, 1680, 1390, 1230 | 2.83(2H, t), 4.08(2H, t), 7.03–7.92(7H, m) | 86.0–91.0 |
| 68 | [3-chlorophenyl] | 1695, 1660, 1380, 1220 | 2.82(2H, t), 4.22(2H, t), 7.03–7.96(7H, m) | 103.7–108.4 |
| 69 | [4-chlorophenyl] | 1700, 1645, 1480, 1360 | 2.82(2H, t), 4.23(2H, t), 6.96–7.96(7H, m) | 138.2–142.0 |
| 70 | [2-methoxyphenyl] | 1695, 1640, 1460, 1360 | 2.78(2H, t), 3.49(3H, s), 4.31(2H, t), 6.63–7.91(7H, m) | 102.3–107.3 |

TABLE 13-continued
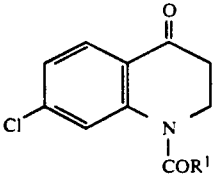
| Ex. No. | R¹ | | NMR(CDCl₃, ppm) | M.P. (°C.) |
|---|---|---|---|---|
| 71 | 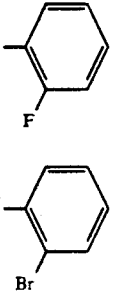 | 1690, 1640, 1480, 1370 | 2.80(2H, t), 4.20(2H, t), 6.83–7.94(7H, m) | 121.8~122.5 |
| 72 | 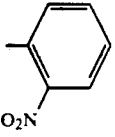 | 1700, 1665, 1380, 1190 | 2.87(2H, t), 4.14(2H, t), 7.04–7.96(7H, m) | 114.1~120.3 |
| 73 | 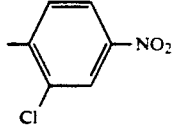 | 1700, 1660, 1570, 1385 | [DMSO-d₆] 2.88(2H, t), 3.99(2H, t), 7.17–8.22(7H, m) | 176.2~176.5 |
| 74 | 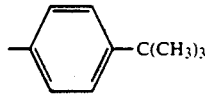 | 1690, 1655, 1395, 1345 | 2.80(2H, t), 4.07(2H, t), 7.07–8.33(6H, m) | 179.6~181.3 |
| 75 | 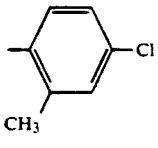 | 1695, 1645, 1455, 1345 | 1.31(9H, s), 2.81(2H, t), 4.21(2H, t), 6.99–7.95 (7H, m) | 124.5~127.6 |
| 76 | 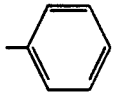 | 1690, 1650, 1370, 900 | 2.31(2H, s), 2.78(2H, t), 4.09(2H, t), 7.02~7.93 (6H, m) | 156.1~160.2 |
| 77 | 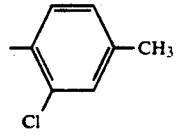 | 1690, 1635, 1475, 1370 | 2.84(2H, t), 4.25(2H, t), 7.04–7.96(8H, m) | 141.7~143.6 |
| 78 | 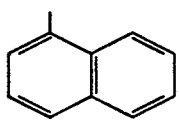 | 1690, 1660, 1465, 1370 | 2.36(3H, s), 2.81(2H, t), 4.09(2H, t), 7.02–7.89(6H, m) | 157.8~158.3 |
| 79 | 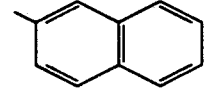 | 1695, 1660, 1460, 1360 | 2.71(2H, t), 4.00(2H, t), 7.01–7.91(10H, m) | 43.2~47.5 |
| 80 | | 1680, 1640, 1460, 1360 | 2.85(2H, t), 4.28(2H, t), 7.00–8.01(10H, m) | 134.0~136.5 |

TABLE 13-continued

[Structure: 7-chloro-1-(COR¹)-2,3-dihydroquinolin-4(1H)-one]

| Ex. No. | R¹ | IR | NMR(CDCl₃, ppm) | M.P. (°C.) |
|---|---|---|---|---|
| 81 | 2-iodophenyl | 1690, 1650, 1460, 1370 | 2.70(2H, t), 3.96(2H, t), 6.95–7.91(7H, m) | 129.4~131.8 |
| 82 | 3-methoxyphenyl | 1690, 1640, 1460, 1355 | 2.82(2H, t), 3.81(3H, s), 4.27(2H, t), 6.95–8.02(7H, m) | 138.6~140.0 |
| 83 | 3-pyridyl | 1690, 1635, 1470, 1360 | [DMSO-d₆+CDCl₃] 2.90(2H, t), 4.21(2H, t), 7.26–7.58(3H, m), 7.90–8.09 2H, m), 8.70–8.86(2H, m) | 175.8~177.8 |
| 84 | 2-pyridyl | 1680, 1650, 1465, 1380 | [DMSO-d₆] 2.86(2H, t), 4.20(2H, t), 7.23–7.62(3H, m), 7.72–8.12 (3H, m), 8.55–8.60(1H, m) | 148.0~149.8 |
| 85 | 4-pyridyl | 1685, 1640, 1490, 1400 | [DMSO-d₆] 2.93(2H, t), 4.10(2H, t), 7.35–8.01(2H, m), 8.07–8.25(2H, m), 8.60–8.82 (1H, m), 8.94–9.02(2H, m) | 171.7~179.2 |
| 86 | pyrazinyl | 1690, 1640, 1480, 1375 | 2.92(2H, t), 4.35(2H, t), 7.15–7.36(2H, m), 8.01 (1H, d), 8.47–8.54(1H, m), 8.77(1H, d), 9.08–9.12(1H, m) | 149.8~151.0 |
| 87 | 2-thienyl | 1690, 1635, 1415, 1365 | 2.87(2H, t), 4.36(2H, t), 6.98–8.03(6H, m) | 94.1~96.1 |
| 88 | 3-thienyl | 1660, 1640, 1475, 1345 | 2.86(2H, t), 4.32(2H, t), 7.11–8.02(6H, m) | 165.1~166.9 |
| | | IR(nujol.cm⁻¹) | | |
| 89 | 4-methylphenyl | 1690, 1650 | | 104~109 |
| 90 | 3-nitrophenyl | 1680, 1660 | | 144~149 |

TABLE 13-continued

[Structure: 7-chloro-2,3-dihydroquinolin-4(1H)-one with N-COR¹ substituent]

| Ex. No. | R¹ | NMR(CDCl₃, ppm) | M.P. (°C.) |
|---|---|---|---|
| 91 | 2-(F₃C)C₆H₄ | 1700, 1665 | 107~109.5 |
| 92 | 3-(CH₃)C₆H₄ | 1685, 1650 | 118~120.3 |
| 93 | 2,3-Cl₂C₆H₃ | 1690, 1650 | 176.5~178.3 |
| 94 | 3,4-(CH₃)₂C₆H₃ | 1690, 1665 | 93~96 |
| 95 | 2,5-Cl₂C₆H₃ | 1695, 1660 | 188~193 |
| 96 | 2,6-F₂C₆H₃ | 1700, 1640 | 111~113.8 |
| 97 | 2-(H₅C₂)C₆H₄ | 1690, 1655 | (Oil) |
| 98 | 2-(H₅C₂O)C₆H₄ | 1690, 1655 | 131~133 |

TABLE 13-continued

[Structure: 7-chloro-3,4-dihydroquinolin-4(1H)-one with N-COR¹ substituent]

| Ex. No. | R¹ | IR (KBr, cm⁻¹) | M.P. (°C.) |
|---|---|---|---|
| 99 | 2,3-dimethoxy-substituted phenyl (H₃CO, OCH₃, OCH₃) | 1685, 1655 | 136.5~140 |
| 100 | 2,3-dimethoxyphenyl (H₃CO, OCH₃) | 1690, 1660 | 136~138.2 |
| 101 | 2,3-dimethylphenyl (H₃C, CH₃) | 1690, 1665 | 143~146.5 |
| 102 | 3-fluorophenyl (F) | 1690, 1640 | 135~136.3 |

TABLE 14

[Structure: 7-R⁶-3,4-dihydroquinolin-4(1H)-one with N-COR¹ substituent]

| Ex. No. | R¹ | R⁶ | IR(KBr, cm⁻¹) | NMR(CDCl₃, ppm) | M.P. (°C.) |
|---|---|---|---|---|---|
| 103 | 2,4-dichlorophenyl | Br | 1690, 1650, 1480, 1380 | 2.80(2H, t), 4.16(2H, t), 7.18-7.89(6H, m) | 181.7~184.5 |
| 104 | 2,4-dichlorophenyl | F | 1695, 1660, 1390, 1230 | 2.80(2H, t), 4.15(2H, t), 6.75-8.09(6H, m) | 120.1~122.9 |
| 105 | —CH₂CH₃ | —OCH₃ | 1690, 1665, 1385, 1245 | 1.21(3H, t), 2.59(2H, q), 2.67(2H, t), 3.84(3H, s), 4.13(2H, t), 6.61-7.95(3H, m) | (Oil) |

TABLE 14-continued
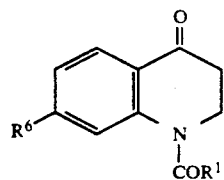
| Ex. No. | R¹ | R⁶ | IR(KBr, cm⁻¹) | NMR(CDCl₃, ppm) | M.P. (°C.) |
|---|---|---|---|---|---|
| 106 | 2,4-diClC₆H₃ | —CH₃ | 1680, 1650, 1465, 1380 | 2.22(3H, s), 2.82(2H, t), 4.18(2H, s), 6.91–7.89(6H, m) | 141.4~145.0 |
| 107 | 2,4-diClC₆H₃ | I | 1690, 1645, 1475, 1380 | 2.82(2H, t), 4.12(2H, t), 7.20–7.70(6H, m) | 186.3~187.9 |
| 108 | 2,4-diClC₆H₃ | —CF₃ | 1790, 1640, 1335, 1175 | 2.90(2H, t), 4.20(2H, t), 7.18–8.11(6H, m) | 136.2~140.2 |
| 109 | 2,4-diClC₆H₃ | —COCH₃ | 1695, 1640, 1420, 1370 | 2.45(3H, s), 2.90(2H, t), 4.25(2H, t), 7.19–8.11(6H, m) | 135.9~139.9 |
| 110 | 2,4-diClC₆H₃ | —OCH₃ | 1680, 1650, 1460, 1380 | 2.83(2H, t), 3.65(3H, s), 4.21(2H, t), 6.61–7.98(6H, m) | 99.6~101.3 |
| 111 | 2,4-diClC₆H₃ | —N(CH₃)₂ | 1670, 1640, 1460, 1365 | 2.80(2H, t), 2.87(6H, s), 4.24(2H, t), 6.38–7.92(6H, m) | 177.7~179.7 |
| 112 | 2,4-diClC₆H₃ | —COOCH₃ | 1720, 1615, 1480, 1390 | 2.80(2H, t), 3.75(3H, s), 4.22(2H, t), 7.16–7.98(6H, m) | 174.9~177.0 |
| 113 | C₆H₅ | F | 1695, 1645, 1480, 1360 | 2.82(2H, t), 4.25(2H, t), 6.67–8.09(8H, m) | 106.8~109.0 |
| 114 | 2,4-diClC₆H₃ | —SCH₃ | 1680, 1640, 1470, 1385 | 2.23(3H, s), 2.82(2H, t), 4.14(2H, t), 6.91–7.91(6H, m) | 113.2~117.2 |

TABLE 14-continued

| Ex. No. | R¹ | R⁶ | IR(KBr, cm⁻¹) | NMR(CDCl$_3$, ppm) | M.P. (°C.) |
|---|---|---|---|---|---|
| 115 | 2,4-dichlorophenyl | —SO$_2$CH$_3$ | 1660, 1380, 1220, 1155 | [DMSO-d$_6$+CDCl$_3$] 2.96(2H, t), 3.02(3H, s), 4.19(2H, t), 7.36-8.16(6H, m) | 191.6~195.6 |
| 116 | 2,4-dichlorophenyl | —SOCH$_3$ | 1660, 1385, 1240, 1055 | 2.55(3H, s), 2.91(2H, t), 4.01(2H, t), 7.33-8.16(6H, m) | 183.3~186.8 |
| 117 | 3-methylphenyl | F | 1660, 1595, 1480, 1360 | 2.34(3H, s), 2.77(2H, t), 4.12(2H, t), 6.73-8.04(7H, m) | 93.5~96.3 |
| 118 | 2,4-dichlorophenyl | —NO$_2$ | 1700, 1660, 1475, 1340 | 2.77(2H, t), 4.02(2H, t), 7.04-7.79(6H, m) | 180.9~183.1 |
| 119 | 3-methylphenyl | —OCH$_3$ | 1680, 1635, 1485, 1370 | 2.27(3H, s), 2.76(2H, t), 3.54(3H, s), 4.25(2H, t), 6.60-8.01(7H, m) | 112.2~116.0 |
| 120 | phenyl | —OCH$_3$ | 1680, 1640, 1440, 1365 | 2.81(2H, t), 3.50(3H, s), 4.32(2H, t), 6.33-8.02(8H, m) | 167.2~168.4 |
| 121 | phenyl | Br | 1690, 1640, 1470, 1370 | 2.84(2H, t), 4.28(2H, t), 7.21-7.89(8H, m) | 153.0~156.7 |
| 122 | 3-methylphenyl | Br | 1695, 1640, 1445, 1370 | 2.33(3H, s), 2.78(2H, t), 4.13(2H, t), 6.98-7.92(7H, m) | 111.7~116.2 |
| 123 | 3-methylphenyl | I | 1695, 1645, 1405, 1375 | 2.32(3H, s), 2.79(2H, t), 4.17(2H, t), 7.19-7.78(7H, m) | 145.4~147.8 |

TABLE 14-continued
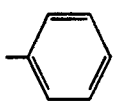
| Ex. No. | R[1] | R[6] | IR(KBr, cm$^{-1}$) | NMR(CDCl$_3$, ppm) | M.P. (°C.) |
|---|---|---|---|---|---|
| 124 | ―⟨phenyl⟩ | I | 1685, 1640, 1460, 1360 | 2.83(2H, t), 4.26(2H, t), 7.18–7.75(8H, m) | 161.8~163.0 |
TABLE 15
| Ex. No. | R[1] | R[2] | R[3] | R[5] | R[6] | IR(KBr, cm$^{-1}$) | NMR(CDCl$_3$, ppm) | M.P. (°C.) |
|---|---|---|---|---|---|---|---|---|
| 125 | ―C(CH$_3$)$_3$ | H | H | Cl | Cl | 1705, 1655, 1460, 1160 | 1.42(9H, s), 2.77(2H, t), 4.17(2H, t), 7.82(1H, s), 7.98(1H, s) | 141.9~146.1 |
| 126 | 2,4-dichlorophenyl | H | H | Cl | Cl | 1700, 1660, 1450, 1390 | 2.78(2H, t), 4.16(2H, t), 7.20–8.02(5H, m) | 153.7~160.6 |
| 127 | 2,4-dichlorophenyl | H | H | F | Cl | 1700, 1650, 1480, 1385 | 2.91(2H, t), 4.10(2H, t), 7.21–7.79 (5H, m) | 162.8~165.5 |
| 128 | phenyl | H | H | F | Cl | 1695, 1640, 1470, 1360 | 2.84(2H, t), 4.25(2H, t), 7.29–7.81 (7H, m) | 152.7~154.8 |
| 129 | 2-methylphenyl | H | H | Cl | Cl | 1695, 1660, 1450, 1380 | [DMSO-d$_6$] 2.33(3H, s), 2.82 (2H, t), 3.97(2H, t), 7.22–7.86 (6H, m) | 135.3~139.1 |
| 130 | phenyl | H | H | Cl | Cl | 1660, 1630, 1440, 1330 | 2.73(2H, t), 4.07(2H, t), 7.21–7.75 (7H, m) | 162.7~163.9 |
| 131 | phenyl | H | H | F | F | 1700, 1660, 1440, 1380 | 2.70(2H, t), 4.02(2H, t), 6.71–7.78 (7H, m) | 130.5~131.7 |

TABLE 15-continued
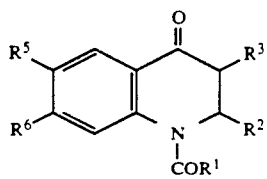
| Ex. No. | R¹ | R² | R³ | R⁵ | R⁶ | IR(KBr, cm⁻¹) | NMR(CDCl₃, ppm) | M.P. (°C.) |
|---|---|---|---|---|---|---|---|---|
| 132 | 2,4-diClC₆H₃ | H | H | F | F | 1700, 1660, 1500, 1395 | 2.69(2H, t), 3.82(2H, t), 6.79-7.40 (5H, m) | 141.8~145.0 |
| 133 | 2-CH₃C₆H₄ | H | H | F | F | 1700, 1650, 1495, 1385 | 2.20(3H, s), 2.67(2H, t), 3.83(2H, t), 6.87-7.69 (6H, m) | 100.4~102.1 |
| 134 | 2-CH₃C₆H₄ | H | H | Br | Cl | 1695, 1660, 1450, 1370 | 2.33(3H, s), 2.78(2H, t), 4.12(2H, t), 7.16-8.26 (6H, m) | 161.7~165.4 |
| 135 | 2,4-diClC₆H₃ | H | H | Br | Cl | 1700, 1660, 1450, 1390 | 2.85(2H, t), 4.11(2H, t), 7.19-8.22 (5H, m) | 191.8~194.7 |
| 136 | 2-CH₃C₆H₄ | H | H | —CH₃ | Cl | 1690, 1655, 1470, 1365 | 2.32(3H, s), 2.35(3H, s), 2.78(2H, t), 4.13(2H, t), 7.18-7.88 (6H, m) | 114.0~119.7 |
| 137 | 2,4-diClC₆H₃ | H | H | —CH₃ | Cl | 1695, 1660, 1470, 1390 | 2.35(3H, s), 2.82(2H, t), 4.13(2H, t), 7.20-7.86 (5H, m) | 123.5~127.5 |
| 138 | C₆H₅ | H | H | Br | Cl | 1700, 1660, 1455, 1370 | 2.82(2H, t), 4.24(2H, t), 7.24-8.21 (7H, m) | 178.1~180.2 |
| 139 | C₆H₅ | H | H | —CH₃ | Cl | 1695, 1650, 1480, 1365 | 2.32(3H, s), 2.80(2H, t), 4.24(2H, t), 7.05-7.82 (7H, m) | 153.8~158.3 |
| 140 | 2-CH₃C₆H₄ | H | H | Cl | F | 1695, 1660, 1480, 1360 | 2.36(3H, s), 2.78(2H, t), 4.12(2H, t), 7.00-8.10 (6H, m) | 83.8~87.9 |

TABLE 15-continued

Structure: quinolinone with R⁵, R⁶ on benzene ring, R³ at 3-position, R² at 2-position, N-COR¹

| Ex. No. | R¹ | R² | R³ | R⁵ | R⁶ | IR(KBr, cm⁻¹) | NMR(CDCl₃, ppm) | M.P. (°C.) |
|---|---|---|---|---|---|---|---|---|
| 141 | 2,4-dichlorophenyl | H | H | Cl | F | 1695, 1660, 1480, 1380 | 2.82(2H, t), 4.08(2H, t), 7.10–8.12 (5H, m) | 116.9–118.9 |
| 142 | 2-methylphenyl | H | H | —OCH₃ | —OCH₃ | 1675, 1640, 1405, 1335 | 2.25(3H, s), 2.78(2H, t), 3.52(3H, s), 3.87(3H, s), 4.24(2H, t), 7.02–7.40 (6H, m) | 179.5–181.3 |
| 143 | —C(CH₃)₃ | —CH₃ | H | Cl | H | 1700, 1660, 1480, 1180 | 1.27(3H, d), 1.40(9H, s), 2.86(2H, d), 4.91(1H, m), 7.36–7.89(3H, m) | 103.1–105.7 |
| 144 | 4-chlorophenyl | —CH₃ | H | Cl | H | 1700, 1650, 1480, 1340 | 1.31(3H, d), 3.00(2H, d), 5.37(1H, m), 6.60–7.91(7H, m) | 131.3–132.7 |

TABLE 16

Structure: 3,4-dihydroquinoline-4(=NOSO₃K) with R⁵ on benzene ring, N-COR¹

| Ex. No. | Compound No. | R¹ | R⁵ | IR(KBr, cm⁻¹) | NMR(DMSO-d₆, ppm) | Decomp. (°C.) |
|---|---|---|---|---|---|---|
| 145 | — | 2,4-dichlorophenyl | 6-Cl | 1650, 1240, 900 | 2.83(2H, t), 3.75(2H, t), 7.13–7.91(6H, m) | 154.0 |
| 146 | — | —OCH₃ | 6-Cl | 1710, 1400, 1250 | 2.78(2H, t), 3.70(3H, s), 3.78(2H, t), 7.31–7.85 (3H, m) | 185.0 |
| 147 | — | —CH₃ | 6-Cl | 1660, 1400, 1240 | 2.21(3H, s), 2.79(2H, t), 3.80(2H, t), 7.40–7.85 (3H, m) | 152.8 |
| 148 | 2 | —CH₂CH₃ | 6-Cl | 1660, 1395, 1285 | 0.97(3H, t), 2.49(2H, q), 2.70(2H, t), 3.74(2H, t), 7.25–7.81(3H, m) | 204.7 |
| 149 | — | —(CH₂)₃CH₃ | 6-Cl | 1660, 1270, 1245 | 0.86(3H, t), 1.27(2H, m), 1.42(2H, m), 2.49(2H, t), 2.76(2H, t), 3.79(2H, t), 7.31–7.86(3H, m) | 137.8 |
| 150 | — | —(CH₂)₇CH₃ | 6-Cl | 1670, 1395, 1260 | 0.87(3H, t), 1.00–1.82 (12H, m), 2.56(2H, t), 2.73(2H, t), 3.77(2H, t), 7.26–7.85(3H, m) | 123.0 |
| 151 | — | —CH₂CH(CH₃)₂ | 6-Cl | 1655, 1390, 1250 | 0.88(6H, d), 2.39(2H, d), 2.72(2H, t), 3.23(1H, m), 3.77(2H, t), 7.26–7.79 | 139.3 |

TABLE 16-continued

[Structure: R⁵-substituted 3,4-dihydroquinoline with =NOSO₃K at 4-position and N-COR¹]

| Ex. No. | Compound No. | R¹ | R⁵ | IR(KBr, cm⁻¹) | NMR(DMSO-d₆, ppm) | Decomp. (°C.) |
|---|---|---|---|---|---|---|
| 152 | — | —C(CH₃)₃ | 6-Cl | 1640, 1405, 1240 | 1.29(9H, s), 2.73(2H, t), 3.83(2H, t), 7.25-7.75 (3H, m) | 170.5 |
| 153 | — | —CH₂CH₂Cl | 6-Cl | 1655, 1400, 1245 | 2.76(2H, t), 3.04(2H, t), 3.06(2H, t), 3.80(2H, t), 7.32-7.86(3H, m) | 192.9 |
| 154 | — | —C(CH₃)₂—CH₂Cl | 6-Cl | 1650, 1400, 1260 | 1.37(6H, s), 2.76(2H, t), 3.78(2H, s), 3.84(2H, t), 7.26-7.75(3H, m) | 187.8 |
| 155 | — | —CH₂CH₂—CO₂CH₃ | 6-Cl | 1740, 1680, 1285 | 2.76(2H, t), 3.29(4H, s), 3.53(3H, s), 3.89(2H, t), 7.32-7.90(3H, m) | 140.7 |
| 156 | — | —CH₂OCH₃ | 6-Cl | 1660, 1410, 1230 | 2.80(2H, t), 3.29(3H, s), 3.73(2H, t), 4.26(2H, s), 7.34-7.89(3H, m) | 210.7 |
| 157 | — |  cyclopropyl | 6-Cl | 1660, 1420, 1260 | 0.89(4H, m), 1.98(1H, m), 2.72(2H, t), 3.86(2H, t), 7.42-7.82(3H, m) | 221.7 |
| 158 | — | 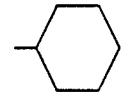 cyclohexyl | 6-Cl | 1650, 1400, 1260 | 1.09-1.87(11H, m), 2.70 (2H, t), 3.79(2H, t), 7.41-7.83(3H, m) | 167.9 |
| 159 | — | —CH₂— 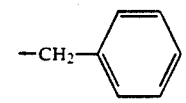 phenyl | 6-Cl | 1660, 1390, 1240 | 2.66(2H, t), 3.79(2H, t), 3.88(2H, s), 7.05-7.79 (8H, m) | 155.7 |
| 160 | — | —CH=CH— 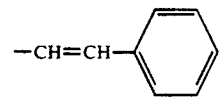 phenyl | 6-Cl | 1650, 1380, 1215 | 2.78(2H, t), 3.90(2H, t), 6.98(1H, d), 7.60(1H, d), 7.30-7.87(8H, m) | 169.5 |
| 161 | — | 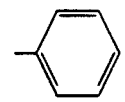 phenyl | 6-Cl | 1645, 1380, 1250 | 2.81(2H, t), 3.82(2H, t), 6.81-7.81(8H, m) | 185.7 |
| 162 | — | 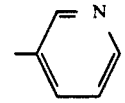 pyridyl | 6-Cl | 1660, 1385, 1280 | 2.86(2H, t), 3.83(2H, t), 6.89-8.52(7H, m) | 231.8 |
| 163 | — | 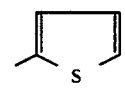 thienyl | 6-Cl | 1640, 1420, 1280 | 2.83(2H, t), 3.93(2H, t), 6.90-7.30(4H, m), 7.66-7.85(2H, m) | 199.4 |
| 164 | — | 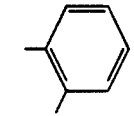 2-methoxyphenyl | 6-Cl | 1640, 1480, 1280 | 2.82(2H, t), 3.46(3H, s), 3.63(2H, t), 6.80-7.85 (7H, m) | 107.2 |
| 165 | — | 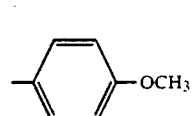 4-methoxyphenyl | 6-Cl | 1640, 1380, 1250 | 2.81(2H, t), 3.70(3H, s), 3.83(2H, t), 6.70-7.76 (7H, m) | 130.1 |

TABLE 16-continued
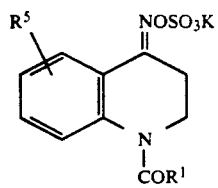
| Ex. No. | Compound No. | R¹ | R⁵ | IR(KBr, cm⁻¹) | NMR(DMSO-d₆, ppm) | Decomp. (°C.) |
|---|---|---|---|---|---|---|
| 166 | — | 2-Cl-phenyl | 6-Cl | 1655, 1480, 1240 | 2.82(2H, t), 3.62(2H, t), 7.15-7.90(7H, m) | 151.8 |
| 167 | 9 | 4-Cl-phenyl | 6-Cl | 1655, 1380, 1280 | 2.83(2H, t), 3.82(2H, t), 6.78-7.80(7H, m) | 207.3 |
| 168 | — | —CH₂CH₃ | 6-Br | 1660, 1400, 1260 | 1.02(3H, t), 2.47(2H, q), 2.73(2H, t), 3.76(2H, t), 7.45-7.92(3H, m) | 206.8 |
| 169 | — | 2,4-diCl-phenyl | 6-F | 1655, 1495, 1280 | 2.81(2H, t), 3.53(2H, t), 7.29-7.67(6H, m) | 159.0 |
| 170 | — | —CH₂CH₃ | 6-OCH₃ | 1640, 1400, 1245 | 1.01(3H, t), 2.47(2H, q), 2.71(2H, t), 3.72(2H, t), 3.76(3H, s), 6.83-7.45 (3H, m) | 159.6 |
| 171 | — | —CH₂CH₃ | 6-H | 1660, 1400, 1250 | 0.99(3H, t), 2.43(2H, q), 2.72(2H, t), 3.73(2H, t), 7.12-7.89(4H, m) | 90.5 |
| 172 | — | 4-Cl-phenyl | 5-Cl | 1650, 1450, 1250 | 2.93(2H, t), 3.80(2H, t), 6.60-7.45(7H, m) | 229.0 |
| 173 | — | —CH₂CH₃ | 5-Cl | 1655, 1395, 1250 | 1.00(3H, t), 2.44(2H, q), 2.83(2H, t), 3.69(2H, t), 7.32(3H, m) | 126.2 |
| 174 | 1 | —C(CH₃)₃ | 5-Cl | 1650, 1400, 1270 | 1.23(9H, s), 2.83(2H, t), 3.77(2H, t), 7.25(3H, m) | 178.0 |
| 175 | — | 2-CH₃-phenyl | 5-Cl | 1650, 1380, 1240 | 2.24(3H, s), 2.97(2H, t), 3.80(2H, t), 6.86-7.44(7H, m) | 146.2 |
| 176 | — | 3-CH₃-phenyl | 6-Cl | 1640, 1370, 1235 | 2.23(3H, s), 2.84(2H, t), 3.82(2H, t), 6.97-7.96(7H, m) | 174.7 |

TABLE 17

Structure: quinoline derivative with =NOSO$_3$K at 4-position, R$^6$ on benzene ring, N-COR$^1$

| Ex. No. | Compound No. | R$^1$ | R$^6$ | IR(KBr, cm$^{-1}$) | NMR(DMSO-d$_6$, ppm) | Decomp. (°C.) |
|---|---|---|---|---|---|---|
| 177 | — | 2,4-dichlorophenyl | 8-Cl | 1665, 1395, 1250 | 2.82(2H, t), 3.55(2H, t), 7.05–7.95(6H, m) | 207.0 |
| 178 | — | —CH$_2$CH$_3$ | 8-Cl | 1660, 1380, 1240 | 0.99(3H, t), 2.47(2H, q), 2.74(2H, t), 3.48(2H, t), 7.10–7.85(3H, m) | 150.0 |
| 179 | 5 | —C(CH$_3$)$_3$ | 8-Cl | 1660, 1280, 1250 | 1.32(9H, s), 2.77(2H, t), 3.80(2H, t), 7.05–7.82 (3H, m) | 187.6 |
| 180 | — | 4-chlorophenyl | 8-Cl | 1650, 1450, 1280 | 2.80(2H, t), 3.27(2H, t), 7.12–7.90(7H, m) | 170.6 |
| 181 | 3 | —CH$_2$CH$_3$ | 7-Cl | 1660, 1395, 1245 | 1.02(3H, t), 2.48(2H, q), 2.77(2H, t), 3.76(2H, t), 7.15–7.96(3H, m) | 152.1 |
| 182 | 4 | —C(CH$_3$)$_3$ | 7-Cl | 1650, 1395, 1240 | 1.30(9H, s), 2.76(2H, t), 3.87(2H, t), 7.10–7.90 (3H, m) | 247.3 |
| 183 | — | —C(CH$_3$)$_2$—CH$_2$Cl | 7-Cl | 1660, 1415, 1255 | 1.38(6H, s), 2.77(2H, t), 3.83(2H, s), 3.88(2H, t), 7.10–7.88(3H, m) | 170.6 |
| 184 | — | 2-chlorophenyl | 7-Cl | 1660, 1385, 1240 | 3.84(2H, t), 3.68(2H, t), 7.12–8.00(7H, m) | 154.9 |
| 185 | — | 3-chlorophenyl | 7-Cl | 1660, 1380, 1280 | 2.87(2H, t), 3.79(2H, t), 7.05–7.95(7H, m) | 171.2 |
| 186 | 10 | 4-chlorophenyl | 7-Cl | 1660, 1495, 1280 | 2.83(2H, t), 3.81(2H, t), 6.95–7.91(7H, m) | 111.3 |
| 187 | — | 2-methoxyphenyl | 7-Cl | 1650, 1390, 1250 | 2.80(2H, t), 3.46(3H, s), 4.09(2H, t), 6.79–7.89 (7H, m) | 173.0 |
| 188 | — | 2-fluorophenyl | 7-Cl | 1655, 1385, 1245 | 2.80(2H, t), 3.80(2H, t), 6.90–7.92(7H, m) | 163.5 |

TABLE 17-continued

[Structure: 3,4-dihydroquinoline with =NOSO₃K at 4-position, N-COR¹ at 1-position, R⁶ on ring]

| Ex. No. | Compound No. | R¹ | R⁶ | IR(KBr, cm⁻¹) | NMR(DMSO-d₆, ppm) | Decomp. (°C.) |
|---|---|---|---|---|---|---|
| 189 | 13 | 2-Br-phenyl | 7-Cl | 1670, 1395, 1245 | 2.84(2H, t), 3.57(2H, t), 6.95–7.95(7H, m) | 205.5 |
| 190 | — | 2-O₂N-phenyl | 7-Cl | 1670, 1520, 1235 | 2.81(2H, t), 3.70(2H, t), 7.10–8.30(7H, m) | 248.1 |
| 191 | 12 | 3-Cl-4-NO₂-phenyl | 7-Cl | 1660, 1530, 1240 | 2.79(2H, t), 3.47(2H, t), 7.09–8.40(6H, m) | 190.5 |
| 192 | — | 2,4-di-Cl-phenyl | 7-Br | 1670, 1400, 1250 | 2.86(2H, t), 3.64(2H, t), 7.24–7.86(6H, m) | 206.2 |
| 193 | 7 | 2,4-di-Cl-phenyl | 7-F | 1660, 1395, 1240 | 2.80(2H, t), 3.59(2H, t), 6.80–8.00(6H, m) | 159.5 |
| 194 | — | —CH₂CH₃ | 7-OCH₃ | 1660, 1390, 1240 | 1.02(3H, t), 2.52(2H, q), 2.71(2H, t), 3.72(2H, t), 3.77(3H, s), 6.69–7.85 (3H, m) | 149.5 |
| 195 | — | 4-C(CH₃)₃-phenyl | 7-Cl | 1645, 1370, 1245 | 1.29(9H, s), 2.81(2H, t), 3.82(2H, t), 6.96–7.92(7H, m) | 193.5 |
| 196 | 21 | 4-Cl-2-CH₃-phenyl | 7-Cl | 1670, 1390, 1225 | 2.21(3H, s), 2.80(2H, t), 3.69(2H, t), 7.09–7.91(6H, m) | 184.7 |
| 197 | — | phenyl | 7-Cl | 1670, 1375, 1255 | 2.85(2H, t), 3.87(2H, t), 6.99–7.98(8H, m) | 166.7 |
| 198 | — | 3-Cl-4-CH₃-phenyl | 7-Cl | 1660, 1390, 1240 | 2.30(3H, s), 2.80(2H, t), 3.70(2H, t), 7.11–7.90(6H, m) | 195.2 |

TABLE 17-continued
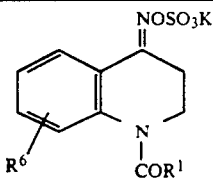
| Ex. No. | Compound No. | R¹ | R⁶ | IR(KBr, cm⁻¹) | NMR(DMSO-d₆, ppm) | Decomp. (°C.) |
|---|---|---|---|---|---|---|
| 199 | — | 1-methylnaphthyl | 7-Cl | 1650, 1370 1240 | 2.78(2H, t), 3.66(2H, t), 7.02–7.87(10H, m) | 169.7 |
| 200 | — | 2-methylnaphthyl | 7-Cl | 1650, 1380 1255 | 2.87(2H, t), 3.86(2H, t), 7.01–7.96(10H, m) | 188.2 |
| 201 | — | 2-iodophenyl | 7-Cl | 1660, 1385, 1240 | 2.89(2H, t), 3.60(2H, t), 7.06–7.98 (7H, m) | 170.0 |
| 202 | — | 3,4-dichlorophenyl | 7-CH₃ | 1655, 1395, 1240 | 2.15(3H, s), 2.82(2H, t), 3.70(2H, t), 6.85–7.83(6H, m) | 158.6 |
| 203 | — | 3,4-dichlorophenyl | 7-I | 1650, 1400, 1240 | 2.87(2H, t), 3.79(2H, t), 7.30–7.88(6H, m) | 190.4 |
| 204 | — | 3,4-dichlorophenyl | 7-CF₃ | 1640, 1380, 1210 | 2.89(2H, t), 3.70(2H, t), 7.29–8.17(6H, m) | 179.7 |
| 205 | — | 3,4-dichlorophenyl | 7-COCH₃ | 1655, 1395, 1220 | 1.99(3H, s), 2.88(2H, t), 4.07(2H, t), 7.30–7.91(6H, m) | 160.4 |
| 206 | — | 3,4-dichlorophenyl | 7-OCH₃ | 1650, 1400, 1250 | 2.84(2H, t), 3.50(3H, s), 3.75(2H, t), 6.60–7.81(6H, m) | 149.8 |
| 207 | — | 3,4-dichlorophenyl | 7-N(CH₃)₂ | 1640, 1395, 1215 | 2.72(6H, s), 2.80(2H, t), 3.89(2H, t), 6.47–7.79(6H, m) | 188.6 |

TABLE 17-continued
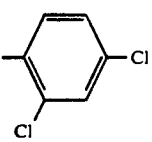
| Ex. No. | Compound No. | R¹ | R⁶ | IR(KBr, cm⁻¹) | NMR(DMSO-d₆, ppm) | Decomp. (°C.) |
|---|---|---|---|---|---|---|
| 208 | — | 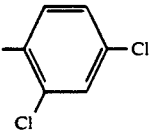 2,4-Cl₂-phenyl | 7-CO₂—CH₃ | 1725, 1655, 1395, 1260 | 2.83(2H, t), 3.72(2H, t), 3.78(3H, s), 7.38-8.06(6H, m) | 182.2 |
| 209 | — |  2,4-Cl₂-phenyl | 7-OH | 1604, 1405, 1240 | 2.76(2H, t), 3.72(2H, t), 6.45-7.69(6H, m) | 209.6 |
| 210 | — | 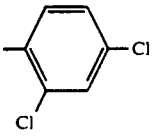 phenyl | 7-F | 1660, 1385, 1250 | 2.80(2H, t), 3.78(2H, t), 6.57-7.89(8H, m) | 148.9 |
| 211 | — | 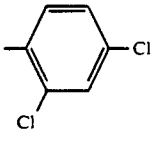 2,4-Cl₂-phenyl | 7-SCH₃ | 1650, 1390, 1240 | 2.21(3H, s), 2.90(2H, t), 3.70(2H, t), 7.00-7.90(6H, m) | 177.7 |
| 212 | — | 2,4-Cl₂-phenyl | 7-SO₂—CH₃ | 1655, 1405, 1235 | 2.97(2H, t), 3.06(3H, s), 3.73(2H, t), 7.45-8.17(6H, m) | 191.5 |
| 213 | — | 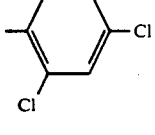 2,4-Cl₂-phenyl | 7-SO₂—CH₃ | 1650, 1390, 1240 | 2.61(3H, s), 3.11(2H, t), 3.92(2H, t), 7.45-8.16(6H, m) | 172.3 |
| 214 | — | 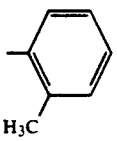 3-CH₃-phenyl | 7-F | 1660, 1380, 1250 | 2.22(3H, s), 2.83(2H, t), 3.79(2H, t), 6.95-8.07(7H, m) | 179.3 |
| 215 | — | 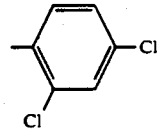 2,4-Cl₂-phenyl | 7-NO₂ | 1640, 1405, 1260 | 2.95(2H, t), 2.78(2H, t), 7.50-8.32 (6H, m) | 226.6 |
| 216 | — | 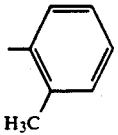 3-CH₃-phenyl | 7-OH | 1610, 1390, 1240 | 2.23(3H, s), 2.79(2H, t), 3.76(2H, t), 6.56-7.82(7H, m) | 196.7 |

TABLE 17-continued

Structure: quinoline derivative with =NOSO₃K at C4, R⁶ at C7, and N-COR¹

| Ex. No. | Compound No. | R¹ | R⁶ | IR(KBr, cm⁻¹) | NMR(DMSO-d₆, ppm) | Decomp. (°C.) |
|---|---|---|---|---|---|---|
| 217 | — | phenyl | 7-OH | 1610, 1395, 1245 | 2.82(2H, t), 3.85(2H, t), 6.29–7.80(8H, m), 9.68(1H, s) | 182.7 |
| 218 | — | 3-methoxyphenyl | 7-Cl | 1645, 1480, 1260 | 2.87(2H, t), 3.77(3H, s), 3.87(2H, t), 6.94–8.02(7H, m) | 189.4 |
| 219 | — | 3-hydroxyphenyl | 7-Cl | 1635, 1390, 1240 | 2.88(2H, t), 3.88(2H, t), 6.81–7.98(7H, m) | 205.2 |
| 220 | — | phenyl | 7-Br | 1645, 1380, 1245 | 2.88(2H, t), 3.88(2H, t), 7.22–7.95(8H, m) | 168.4 |
| 221 | — | 2-methylphenyl | 7-Br | 1655, 1380, 1225 | 2.22(3H, s), 2.83(2H, t), 3.78(2H, t), 7.24–7.92(7H, m) | 197.9 |
| 222 | — | 3-pyridyl | 7-Cl | 1655, 1395, 1215 | 2.93(2H, t), 3.90(2H, t), 7.20–7.62(3H, m), 7.95–8.06(2H, m), 8.70–8.77(2H, m) | 208.9 |
| 223 | — | 2-pyridyl | 7-Cl | 1650, 1385, 1250 | 2.89(2H, t), 3.90(2H, t), 7.11–7.58(3H, m), 7.74–8.08(3H, m), 8.53–8.77(1H, m) | 190.2 |
| 224 | — | 4-pyridyl | 7-Cl | 1640, 1405, 1225 | 2.91(2H, t), 3.80(2H, t), 7.24–7.53(2H, m), 7.90–8.09(3H, m), 8.88–8.98(2H, m) | 242.0 |
| 225 | — | 2,5-dimethylphenyl | 7-I | 1650, 1375, 1240 | 2.22(3H, s), 2.82(2H, t), 3.76(2H, t), 7.17–7.79(7H, m) | 174.2 |
| 226 | — | phenyl | 7-I | 1640, 1360, 1240 | 2.87(2H, t), 3.87(2H, t), 7.19–7.77(8H, m) | 194.1 |

TABLE 17-continued

Structure:

4-(NOSO₃K)=N, 2,3-dihydroquinoline with N-COR¹ at position 1 and R⁶ substituent on benzene ring.

| Ex. No. | Compound No. | R¹ | R⁶ | IR(KBr, cm⁻¹) | NMR(DMSO-$d_6$, ppm) | Decomp. (°C.) |
|---|---|---|---|---|---|---|
| 227 | — | 2-methylphenyl | 8-Cl | 1650, 1370, 1245 | 2.42(3H, s), 3.84(2H, t), 3.55(2H, t), 7.12–7.98(7H, m) | 179.2 |
| 228 | — | pyrazin-2-yl | 7-Cl | 1660, 1380, 1250 | 2.90(2H, t), 3.93(2H, t), 7.22–7.33(2H, m), 7.95 (1H, d), 8.59–8.63(1H, m), 8.75(1H, d), 8.97–9.04 (1H, m) | 174.6 |
| 229 | — | thiophen-2-yl | 7-Cl | 1640, 1405, 1240 | 2.89(2H, t), 4.00(2H, t), 7.05–8.03(6H, m). | 160.7 |
| 230 | — | thiophen-3-yl | 7-Cl | 1640, 1405, 1240 | 2.87(2H, t), 3.93(2H, t), 7.09–8.02(6H, m) | 155.8 |
| 231 | — | 4-methylphenyl | 7-Cl | 1665, 1400, 1365, 1255 | 2.85(2H, t), 2.34(3H, s), 3.86(2H, t), 7.08–8.02(7H, m)* | 192.0 |
| 232 | — | 3-nitrophenyl | 7-Cl | 1660, 1350, 1250 | 2.90(2H, t), 3.87(2H, t), 7.19–8.36(7H, m)* | 168.0 |
| 233 | — | 2-trifluoromethylphenyl | 7-Cl | 1655, 1410, 1220 | 2.89(2H, t), 3.69(2H, t), 7.23–8.28(7H, m).* | 232.0 |
| 234 | — | 3-methylphenyl | 7-Cl | 1670, 1365, 1255 | 2.85(2H, t), 2.32(3H, s), 3.86(2H, t), 7.14–8.26(7H, m)* | 134.0 |
| 235 | — | 2,3-dichlorophenyl | 7-Cl | 1670, 1415, 1390, 1255 | 2.85(2H, t), 3.68(2H, t), 7.22–8.27(6H, m)* | 203.0 |
| 236 | — | 3,4-dimethylphenyl | 7-Cl | 1660, 1375, 1245 | 2.20(3H, s), 2.30(3H, s), 2.82(2H, t), 3.76(2H, t), 7.09–8.03(6H, m)* | 138.0 |

TABLE 17-continued

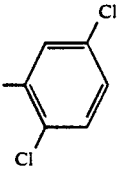

| Ex. No. | Compound No. | R[1] | R[6] | IR(KBr, cm$^{-1}$) | NMR(DMSO-d$_6$, ppm) | Decomp. (°C.) |
|---|---|---|---|---|---|---|
| 237 | — | 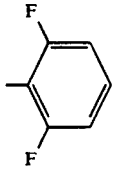 2,5-dichlorophenyl | 7-Cl | 1660, 1405, 1230 | 2.84(2H, t), 3.56(2H, t), 7.17–8.13(6H, m)* | 177.8 |
| 238 | 22 | 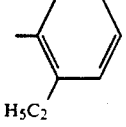 2,6-difluorophenyl | 7-Cl | 1660, 1380, 1270 | 2.83(2H, t), 3.56(2H, t), 7.03–8.02(6H, m)* | 185.0 |
| 239 | 24 | 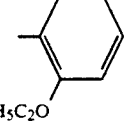 2-ethylphenyl | 7-Cl | 1660, 1375, 1240 | 1.14(3H, t), 2.59(2H, q), 2.80(2H, t), 3.73(2H, t), 6.91–8.02(7H, m)* | 175.9 |
| 240 | — | 2-ethoxyphenyl | 7-Cl | 1650, 1385, 1245 | 1.25(3H, t), 2.90(2H, t), 3.76(2H, q), 3.76(2H, t), 6.87–7.99(7H, m)* | 138.0 |
| 241 | — | 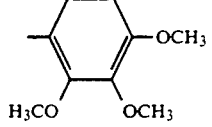 2,3,4-trimethoxyphenyl | 7-Cl | 1650, 1415, 1380, 1280 | 2.83(2H, t), 3.65(6H, s), 3.83(3H, s), 6.77–7.99(5H, m)* | 129.0 |
| 242 | 23 | 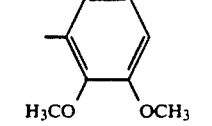 2,6-dimethoxyphenyl | 7-Cl | 1660, 1385 1270 | 2.81(2H, t), 3.64(3H, s), 3.80(3H, s), 6.84–8.01(6H, m)* | 127.0 |
| 243 | — | 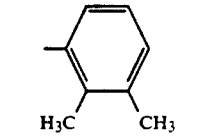 2,6-dimethylphenyl | 7-Cl | 1660, 1380, 1250 | 2.14(3H, s), 2.25(3H, s), 2.80(2H, t), 3.71(2H, t), 7.16–8.03(6H, m)* | 151.0 |
| 244 | — | 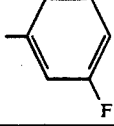 3-fluorophenyl | 7-Cl | 1655, 1380, 1255 | 2.87(2H, t), 3.85(2H, t), 7.16–8.04(7H, m)* | 116.0 |

NMR spectral data obtained at 60 MHz are marked with an asterisk(*).

TABLE 18
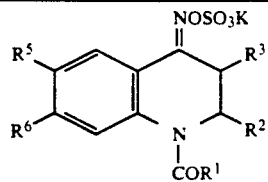
| Ex. No. | Compound No. | R¹ | R² | R³ | R⁵ | R⁶ | IR(KBr, cm⁻¹) | NMR(DMSO-d₆, ppm) | Decomp. (°C.) |
|---|---|---|---|---|---|---|---|---|---|
| 245 | 17 | 2,4-diClC₆H₃ | H | H | Cl | Cl | 1660, 1395, 1245 | 2.79(2H, t), 3.53(2H, t), 7.29–7.93, (5H, m) | 137.5 |
| 246 | — | 4-ClC₆H₄ | —CH₃ | H | Cl | H | 1620, 1480, 1260 | 0.99(3H, d), 2.81(2H, d), 4.82(1H, m), 7.05–7.82 (7H, m) | 168.7 |
| 247 | 16 | —C(CH₃)₃ | —CH₃ | H | Cl | H | 1650, 1410, 1280 | 1.01(3H, d), 1.30(9H, s), 2.74(2H, d), 4.82(1H, m), 7.28–7.80 (3H, m) | 159.6 |
| 248 | 8 | 2,4-diClC₆H₃ | H | —CH₃ | Cl | H | 1650, 1395, 1280 | 1.10(3H, d), 3.48(2H, d), 3.60(1H, m), 7.15–7.85 (6H, m) | 196.7 |
| 249 | — | 2,4-diClC₆H₃ | H | H | F | Cl | 1665, 1395, 1240 | 2.83(2H, t), 3.55(2H, t), 7.34–7.73 (5H, m) | 221.7 |
| 250 | — | 2,4-diClC₆H₃ | H | H | H | H | 1650, 1400, 1240 | 2.88(2H, t), 3.79(2H, t), 7.01–7.98 (7H, m) | 191.8 |
| 251 | 19 | C₆H₅ | H | H | F | Cl | 1665, 1400, 1235 | 2.85(2H, t), 3.84(2H, t), 7.22–7.76 (7H, m) | 212.3 |
| 252 | — | 2-CH₃C₆H₄ | H | H | Cl | Cl | 1660, 1380, 1225 | 2.29(3H, s), 2.81(2H, t), 3.78(2H, t), 7.05–8.98 (6H, m) | 200.6 |
| 253 | — | C₆H₅ | H | H | Cl | Cl | 1660, 1380, 1225 | 2.77(2H, t), 3.72(2H, t), 7.19–7.80 (7H, m) | 217.8 |
| 254 | — | C₆H₅ | H | H | F | F | 1660, 1400, 1240 | 2.85(2H, t), 3.85(2H, t), 7.02–7.90 (7H, m) | 181.1 |

TABLE 18-continued

Structure:
$R^5$, $R^6$ on benzene ring fused to N-containing ring; substituent =NOSO$_3$K, $R^3$, $R^2$; N-COR$^1$

| Ex. No. | Compound No. | R$^1$ | R$^2$ | R$^3$ | R$^5$ | R$^6$ | IR(KBr, cm$^{-1}$) | NMR(DMSO-d$_6$, ppm) | Decomp. (°C.) |
|---|---|---|---|---|---|---|---|---|---|
| 255 | — | 2,4-diCl-phenyl | H | H | F | F | 1660, 1405, 1255 | 2.85(2H, t), 3.55(2H, t), 7.49–7.91 (5H, m) | 160.4 |
| 256 | — | 2-CH$_3$-phenyl | H | H | F | F | 1660, 1390, 1250 | 2.26(3H, s), 2.82(2H, t), 3.73(2H, t), 7.06–7.96 (6H, m) | 162.1 |
| 257 | — | 2-CH$_3$-phenyl | H | H | Br | Cl | 1655, 1380, 1240 | 2.28(3H, s), 2.90(2H, t), 3.81(2H, t), 7.26–8.27 (6H, m) | 162.5 |
| 258 | — | 2,4-diCl-phenyl | H | H | Br | Cl | 1660, 1385, 1230 | 2.86(2H, t), 3.69(2H, t), 7.47–8.15 (5H, m) | 164.5 |
| 259 | 20 | 2-CH$_3$-phenyl | H | H | —CH$_3$ | Cl | 1645, 1380, 1240 | 2.20(3H, s), 2.30(3H, s), 2.81(2H, t), 3.76(2H, t), 7.04–7.86 (6H, m) | 183.5 |
| 260 | — | 2,4-diCl-phenyl | H | H | —CH$_3$ | Cl | 1670, 1395, 1240 | 2.33(3H, s), 2.86(2H, t), 3.61(2H, t), 7.38–7.87 (5H, m) | 218.5 |
| 261 | — | phenyl | H | H | Br | Cl | 1660, 1380, 1245 | 2.87(2H, t), 3.87(2H, t), 7.30–8.20 (7H, m) | 211.5 |
| 262 | — | phenyl | H | H | —CH$_3$ | Cl | 1655, 1370, 1255 | 2.32(3H, s), 2.86(2H, t), 3.86(2H, t), 7.05–7.89 (7H, m) | 202.8 |
| 263 | — | 3-CH$_3$-phenyl | H | H | Cl | F | 1665, 1380, 1240 | 2.24(3H, s), 2.83(2H, t), 3.78(2H, t), 7.05–8.06 (6H, m) | 179.3 |

TABLE 18-continued

![structure with NOSO3K oxime on quinoline]

| Ex. No. | Compound No. | R¹ | R² | R³ | R⁵ | R⁶ | IR(KBr, cm⁻¹) | NMR(DMSO-d₆, ppm) | Decomp. (°C.) |
|---|---|---|---|---|---|---|---|---|---|
| 264 | — | 2,4-dichlorophenyl | H | H | Cl | F | 1655, 1390, 1240 | 2.84(2H, t), 3.69(2H, t), 7.42–8.09 (5H, m) | 185.5 |
| 265 | — | 2-methylphenyl | H | H | —O—CH₃ | —O—CH₃ | 1620, 1400, 1260 | 2.15(3H, s), 2.84(2H, t), 3.25(3H, s), 3.76(3H, s), 3.91(2H, t), 7.12–7.34 (6H, m) | 164.6 |
| 266 | — | 3-methylphenyl | H | H | H | H | 1625, 1375, 1040 | 2.21(3H, s), 2.85(2H, t), 3.82(2H, t), 6.99–7.99 (8H, m) | 136.9 |

Now, typical but non-limiting examples of formulations of the compound of this invention will be shown below.

Formulation A (Capsules)

Compound 6, 40 g of weight, 645 g of lactose and 15 g of magnesium stearate were weighed and mixed until the mixture became homogeneous. The mixture was then filled in No. 1 hard gelatin capsule at 350 mg each to obtain capsule preparation.

Formulation B (Tablets)

Compound 6, 50 g of weight, 800 g of lactose, 120 g of poteto starch, 15 g of polyvinyl alcohol and 15 g of magnesium stearate were weighed. The weighed amount of compound 6, lactose and potato starch were mixed until accomplishing homogeneity. Then aqueous solution of polyvinylalcohol was added to the mixture and granulated by wet process. The granules were then dried, mixed with magnesium stearate and pressed into tablets, each weighing 200 mg.

Formulation C (Powder)

Compound 11, 100 g of weight, 890 g of lactose and 10 g of magnesium stearate were weighed and mixed until 10 g of magnesium stearate were weighed and mixed until the mixture became homogeneous to obtain 10% powder preparation.

Formulation D (Rectal suppository)

Compound 4, 100 g of weight, 180 g of polyethyleneglycol 1500, 720 g of polyethyleneglycol 4000 were ground well in a mortar and formulated into suppository by melting and casting in appropriate mold.

Formulation E (Injection)

Compound 11, 1 g of weight, was weighed and dissolved in 200 ml of distilled water for injection. The solution was filtered, sterilized. Two milliliters each of the sterilized solution was poured into 5-ml ampoules and sealed to obtain preparation for injection.

What is claimed is:

1. An intermediate compound in the synthesis of 1-acyl-2,3-dihydro-4(1H)-quinolinone-4-oxime derivative, said intermediate compound being a 1-acyl-2,3-dihydro-4(1H)-quinolinone compound represented by the formula (IV):

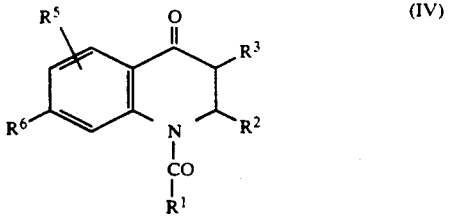

(IV)

wherein R¹ represents a naphthyl, a thienyl, a phenyl or a phenyl substituted with 1 to 5 substituents which are the same or different and selected from a group consisting of an alkyl of straight or branched chain having from 1 to 4 carbon atoms, a hydroxyl, a nitro, a lower alkyloxy, a trifluoromethyl and a halogen atom, provided that the summation of nitro or iodo atoms is not greater than three, R² and R³ are the same or different and represent hydrogen atoms or methyl, R⁵ represents a hydrogen atom, a halogen atom, a hydroxyl, a methylthio, a methylsulfinyl, a methanesulfonyl, an N, N-dimethylamino, a nitro, an acetyl, a methyl, a trifluoromethyl, a methoxycarbonyl or a methoxy and R⁶ represents a halogen atom, a hydroxyl, a methylthio, a methylsulfinyl, a methanesulfonyl, an N,N-dimethylamino, a nitro, an acetyl, a methyl, a trifluoromethyl, a methoxycarbonyl or a methoxy.

2. An intermediate compound as claimed in claim 1 wherein $R^6$ represents a halogen atom.

3. An intermediate compound as claimed in claim 2 wherein $R^1$ represents a phenyl.

4. An intermediate compound as claimed in claim 2 wherein $R^1$ represents a 2-halophenyl.

5. An intermediate compound as claimed in claim 2 wherein $R^1$ represents a 2-methylphenyl.

6. An intermediate compound as claimed in claim 2 wherein $R^1$ represents a 2-ethylphenyl.

7. An intermediate compound as claimed in claim 2 wherein $R^1$ represents a 2-trifluoromethylphenyl.

8. An intermediate compound as claimed in claim 2 wherein $R^1$ represents a 2-methoxyphenyl.

9. An intermediate compound as claimed in claim 2 wherein $R^1$ represents a 2-nitrophenyl.

10. An intermediate compound as claimed in claim 2 wherein $R^1$ represents a 4-chlorophenyl.

11. An intermediate compound as claimed in claim 2 wherein $R^1$ represents a 2,4-dichlorophenyl.

12. An intermediate compound as claimed in claim 2 wherein $R^1$ represents a 2,4-dimethylphenyl.

13. An intermediate compound as claimed in claim 2 wherein $R^1$ represents a 2,6-difluorophenyl.

14. An intermediate compound as claimed in claim 2 wherein $R^1$ represents a 2,3-dimethoxyphenyl.

15. An intermediate compound as claimed in claim 2 wherein $R^1$ represents a 4-chloro-2-methylphenyl.

* * * * *